US012734206B2

(12) United States Patent
Jang et al.

(10) Patent No.: US 12,734,206 B2
(45) Date of Patent: Sep. 15, 2026

(54) COMPOSITION FOR HANGOVER RELIEF COMPRISING NONI FRUIT EXTRACT OR FRACTION THEREOF AND USE THEREOF

(71) Applicant: COSMAX NBT, INC., Gyeonggi-do (KR)

(72) Inventors: Ji Hwan Jang, Gyeonggi-do (KR); Min Son Kweon, Seoul (KR); Su Young Choi, Gyeonggi-do (KR)

(73) Assignee: COSMAX NBT, INC., Gyeonggi-do (KR)

( * ) Notice: Subject to any disclaimer, the term of this patent is extended or adjusted under 35 U.S.C. 154(b) by 426 days.

(21) Appl. No.: 18/037,527

(22) PCT Filed: Nov. 17, 2021

(86) PCT No.: PCT/KR2021/016932
§ 371 (c)(1),
(2) Date: May 17, 2023

(87) PCT Pub. No.: WO2022/108343
PCT Pub. Date: May 27, 2022

(65) Prior Publication Data

US 2024/0016876 A1 Jan. 18, 2024

(30) Foreign Application Priority Data

Nov. 17, 2020 (KR) ........................ 10-2020-0153785
Nov. 8, 2021 (KR) ........................ 10-2021-0152614

(51) Int. Cl.
*A61K 36/746* (2006.01)
*A61K 31/715* (2006.01)
*A61P 43/00* (2006.01)

(52) U.S. Cl.
CPC .......... *A61K 36/746* (2013.01); *A61K 31/715* (2013.01); *A61P 43/00* (2018.01); *A61K 2236/33* (2013.01)

(58) Field of Classification Search
CPC .. A61K 31/715; A61K 36/72; A61K 2236/33; A61K 36/746; A23L 33/105; A23L 2/04
See application file for complete search history.

(56) References Cited

U.S. PATENT DOCUMENTS

| | | | |
|---|---|---|---|
| 11,628,195 | B2 | 4/2023 | Jang et al. |
| 2011/0206787 | A1 | 8/2011 | West et al. |
| 2022/0080018 | A1 | 3/2022 | Jang et al. |

FOREIGN PATENT DOCUMENTS

| | | | |
|---|---|---|---|
| CN | 109198635 | 1/2019 | |
| JP | 2013-520515 | 6/2013 | |
| KR | 10-2009-0072555 | 7/2009 | |
| KR | 10-2012-0126456 | 11/2012 | |
| KR | 10-2012-0134873 | 12/2012 | |
| KR | 10-1322230 | 10/2013 | |
| KR | 10-1949617 | 5/2017 | |
| KR | 10-2062716 | 1/2020 | |
| KR | 10-2082106 | 2/2020 | |
| KR | 102082106 B1 * | 2/2020 | ........... A61K 36/746 |
| KR | 10-2020-0068817 | 6/2020 | |
| KR | 10-2020-0092720 | 8/2020 | |
| WO | WO 2020/153608 | 7/2020 | |

OTHER PUBLICATIONS

Srinivasan et al. Current Res Food Sci I, 2019, 8-16.*
Chang et al., "Hepatoprotection of Noni Juice against Chronic Alcohol Consumption: Lipid Homeostasis, Antioxidation, Alcohol Clearance, and Anti-inflammation," J. Agric. Food Chem. (2013) 61, 11016-11024.
Murata et al., "Activation of cell-mediated immunity by Morinda citrifolia fruit extract and its constituents," Nat Prod Commun. (2014) 9(4): 445-450.
Nayak et al., "Immunostimulant activity of noni (*Morinda citrifolia*) on T and B lymphocytes," Pharm Biol. (2010) 48(7): 724-731.
Tsukamoto et al, "Determinations of ethanol, acetaldehyde and acetate in blood and urine during alcohol oxidation in man," Alcohol Alcohol. (1989) 24(2):101-8.

* cited by examiner

*Primary Examiner* — Kyle A Purdy
(74) *Attorney, Agent, or Firm* — Harness, Dickey & Pierce, P.L.C.

(57) ABSTRACT

The present invention relates to a composition for hangover relief, comprising a noni fruit extract or a fraction thereof, and more specifically provides a noni fruit extract or a fraction thereof, which is prepared using a certain concentration of ethanol as an extraction solvent, to contain a large amount of polysaccharides having excellent hangover relieving functionality and an average molecular weight of 8 kDa to 10 kDa.

3 Claims, 18 Drawing Sheets

Standard product and calibration curve

Purified water fraction of 10% ethanol extract

Standard product and calibration curve

Purified water fraction of 30% ethanol extract

Noni juice

Noni juice crude polysaccharides

Water-saturated butanol fraction of noni extract

Standard product and calibration curve

Fraction 1

Fraction 2

Fraction 3

Fraction 4

Dextran
FIG. 11F
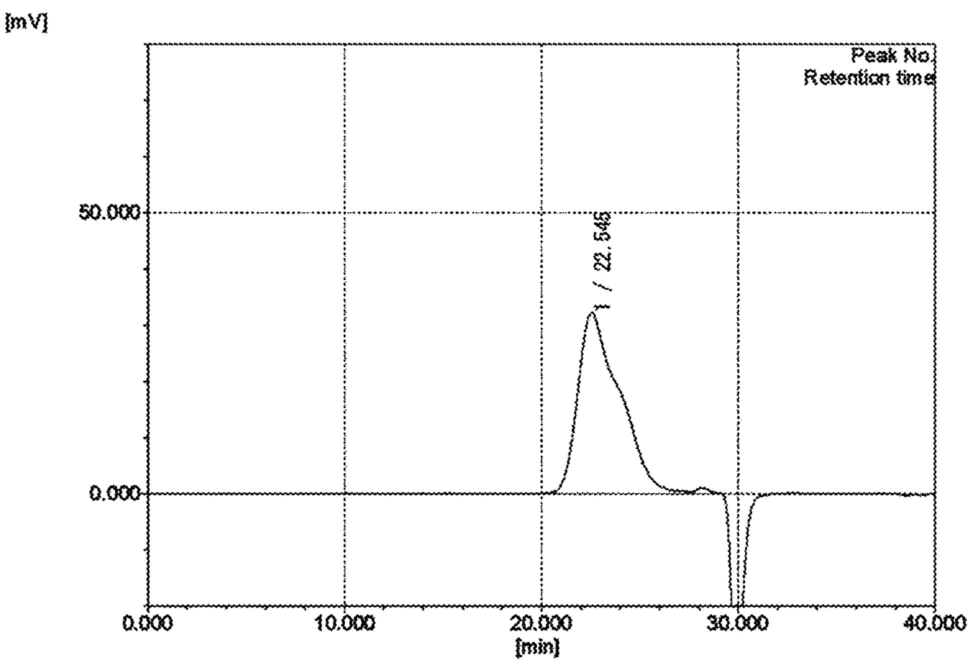
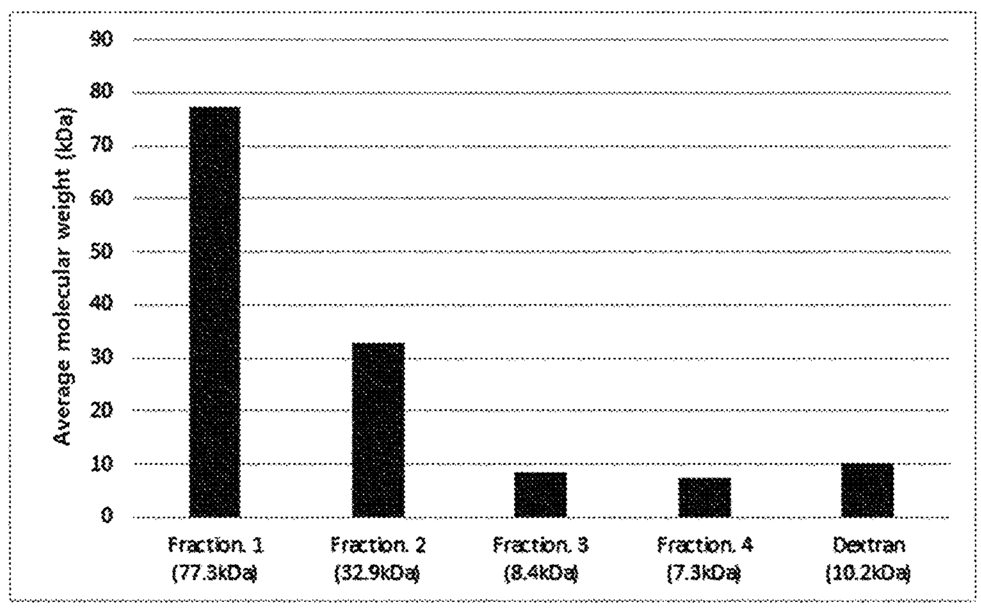
FIG. 12

COMPOSITION FOR HANGOVER RELIEF COMPRISING NONI FRUIT EXTRACT OR FRACTION THEREOF AND USE THEREOF

CROSS REFERENCE TO RELATED APPLICATIONS

This application is a national stage application under 35 U.S.C. § 371 of International Application No. PCT/KR2021/016932, filed internationally on Nov. 17, 2021, which claims priority to and the benefit of Korean Application No. 10-2020-0153785, filed on Nov. 17, 2020 and Korean Application No. 10-2021-0152614, filed on Nov. 8, 2021, the disclosures of which are incorporated herein by reference in their entireties.

TECHNICAL FIELD

The present invention relates to a composition for relieving a hangover including a noni fruit extract or a fraction thereof and use thereof, and more specifically provides a noni fruit extract or a fraction thereof which is prepared to contain a large amount of polysaccharides having an average molecular weight of 8 kDa to 10 kDa with excellent hangover relief functionality, by using a specific concentration of ethanol as an extraction solvent.

BACKGROUND ART

A hangover is a general term for physical and mental discomfort after drinking alcohol, and objective symptoms include nausea, vomiting, drowsiness, headache, decreased exercise capacity, hematological changes and hormonal changes. The degree of hangover varies greatly depending on individual variation according to heredity and the environmental status (nutrition status, exercise status, degree of dehydration, health status).

After drinking, alcohol is metabolized through three pathways, and when the concentration of ethanol is low, it is metabolized by the action of alcohol dehydrogenase (ADH) and acetaldehyde dehydrogenase (ALDH) present in the gastrointestinal tract or liver to acetaldehyde and acetic acid by the microsomal ethanol oxidizing system (MEOS) which is present in the endoplasmic reticulum when the concentration is high, and then, it passes through the action of catalase present in the peroxisome, and it is finally decomposed into carbon dioxide ($CO_2$) and water ($H_2O$). When an appropriate amount of alcohol is introduced, the metabolic system described above works smoothly, and various symptoms caused by alcohol do not occur.

However, when a large amount of alcohol is introduced, as the balance of the metabolic system is disrupted, in vivo homeostasis cannot be maintained, resulting in headaches or heaviness, loss of concentration, heartburn and indigestion in the short term, and liver dysfunction in the long term.

Accordingly, research and experiments on various functional foods or beverages for relieving a hangover are being conducted by targeting various herbal materials. Among these, various hangover relieving drinks using an Oriental raisin tree fruit extract are being developed (Korean Patent Application No. 10-2020-0068817), and Condition (CJ Corporation), which is a representative hangover relieving drink currently on the market, also uses an Oriental raisin tree fruit extract as raw material. In addition, most of the products on the market use various substances with excellent efficacy, including herbal materials, but the overall reliability of the products is low because the amount used is insufficient and objective verification of the efficacy of the final product is insufficient.

Therefore, there is a continuous demand for the development of products that can objectively verify the effect of relieving a hangover and secure consumer trust, as well as reduce social losses due to excessive drinking, thereby helping to lead a healthy life.

Accordingly, the inventors of the present invention have found that when a noni fruit extract is prepared by using a specific concentration of ethanol as an extraction solvent, it contains polysaccharides having an average molecular weight of 8 kDa to 10 kDa, which are the most excellent in enhancing the ADH activity involved in ethanol decomposition in the body, and the present invention was completed by confirming that it is possible to exhibit an excellent hangover relieving effect.

DISCLOSURE

Technical Problem

Accordingly, an object of the present invention is to provide a composition for relieving a hangover and/or a food composition for relieving a hangover using a noni fruit extract or a fraction thereof, which is prepared by using a specific concentration of ethanol as an extraction solvent.

Another object of the present invention is to provide a method for relieving a hangover by using a noni fruit extract or a fraction thereof prepared by using a specific concentration of ethanol as an extraction solvent.

Still another object of the present invention is to provide the use of a noni fruit extract or a fraction thereof which is prepared by using a specific concentration of ethanol as an extraction solvent in the manufacture of a medicament for relieving a hangover.

Technical Solution

In order to solve the above-described problems, the present invention provides a composition for relieving a hangover, including:

- polysaccharide having an average molecular weight of 8 kDa to 10 kDa which is derived from a noni fruit extract; or
- a noni fruit extract or a fraction thereof including polysaccharide having an average molecular weight of 8 kDa to 10 kDa.

According to a preferred exemplary embodiment of the present invention, the noni fruit extract may be prepared by using 10% ethanol as an extraction solvent.

According to another exemplary embodiment of the present invention, the fraction may be a purified water fraction of a noni fruit extract which is extracted with 10% ethanol.

According to still another exemplary embodiment of the present invention, the composition may exhibit the effects of (a) enhancing the activity of alcohol dehydrogenase; (b) enhancing the activity of aldehyde dehydrogenase; (c) reducing blood alcohol concentration; and (d) reducing the concentration of acetaldehyde in the blood.

In addition, the present invention provides a food composition and/or health functional food composition for relieving a hangover, including the above-described composition.

In addition, the present invention provides a method for relieving a hangover, including administering an effective amount of a composition including polysaccharide having an average molecular weight of 8 kDa to 10 kDa which is derived from a noni fruit extract, or a noni fruit extract or a fraction thereof including the polysaccharide to a subject in need thereof.

Additionally, the present invention provides the use of a composition including polysaccharide having an average molecular weight of 8 kDa to 10 kDa which is derived from a noni fruit extract, or a noni fruit extract or a fraction thereof including the polysaccharide in the manufacture of a medicament or food for relieving a hangover.

Advantageous Effects

The noni fruit ethanol extract and a fraction thereof according to the present invention are composed of polysaccharides having an average molecular weight of 8 kDa to 10 kDa, and exhibit superior ADH and/or ALDH activity compared to extracts that are composed of polysaccharides having other average molecular weights, and thus, they have an excellent hangover relieving effect. In addition, since purified water and ethanol are used as extraction solvents, it is the most environmentally friendly and economically feasible in terms of food processing.

DESCRIPTION OF DRAWINGS

FIG. 11*f* shows the GPC results of dextran which is known to have an average molecular weight of 9 to 11 kDa.

FIG. 12 shows the average molecular weight of polysaccharides and the average molecular weight of dextran included in each of the four fractions (Fractions 1 to 4) of FIG. 10.

BEST MODE

Figure 1:
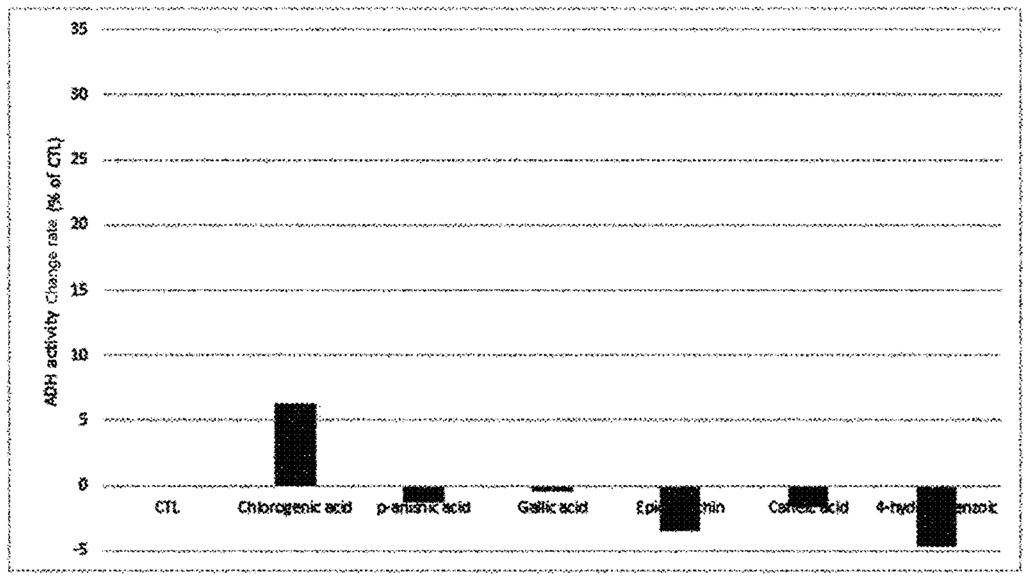
FIG. 1 shows the results of measuring the efficacy of enhancing the activity of alcohol dehydrogenase (ADH) by chlorogenic acid, p-anisic acid, gallic acid, epicatechin, caffeic acid and 4-hydroxybenzoic acid, which are polyphenolic compounds that are known to be included in noni.

As described above, most of the products on the market use a variety of substances with excellent efficacy, including herbal materials, but the amount used is insufficient, and the objective verification of the efficacy of the final product is insufficient, and thus, the reliability of the product is low overall. Accordingly, there is a continuous demand for the development of products that can objectively verify the effectiveness of relieving hangovers and secure the trust of consumers.

Accordingly, the inventors of the present invention have found that when a noni fruit extract is prepared by using a specific concentration of ethanol as an extraction solvent, it contains polysaccharides having an average molecular weight of 8 kDa to 10 kDa, which are the most excellent in enhancing the ADH activity involved in ethanol decomposition in the body, and thus, by confirming that it is possible to exhibit an excellent hangover relieving effect, the inventors of the present invention have sought a solution to the above-mentioned problems.

Accordingly, a first aspect of the present invention relates to composition for relieving a hangover including the following:

polysaccharide having an average molecular weight of 8 kDa to 10 kDa which is derived from a noni fruit extract; or a noni fruit extract or a fraction thereof including polysaccharide having an average molecular weight of 8 kDa to 10 kDa.

As used herein, the term “extract” includes an extract obtained by the extraction of the noni fruit, more preferably, the dried noni fruit, a diluted or concentrated solution of the extract, a dried product obtained by drying the extract, a crude product of the extract, a purified product or a mixture thereof, the extract itself and extracts of all formulations that can be formed by using the extract.

The noni fruit used in the composition of the present invention may be purchased commercially, or harvested or grown in nature, and a noni fruit which is dried naturally or by hot air drying and includes all of pulp, rind and seeds is used.

The noni fruit extract of the present invention may be extracted from a natural, hybrid or mutated plant of the corresponding plant, and it may also be extracted from a plant tissue culture.

In the composition of the present invention, the noni fruit extract may be prepared by using ethanol as an extraction solvent. Extraction using ethanol (i.e., ethanol extraction) is not only the most environmentally friendly and economically feasible extraction method in terms of food processing, but also iridoids can be extracted more efficiently than when other organic solvents such as methanol, hexane, ethyl acetate, methyl chloride or acetone are used as extraction solvents.

In the composition of the present invention, the concentration of ethanol may be 10% to 20%, more preferably, 10% to 15%, and most preferably, 10%.

As used herein, the term "fraction" refers to a result product obtained by performing fractionation in order to separate a specific component or a specific component group from a mixture including various components.

The method for obtaining the fraction in the present invention is not particularly limited, and it may be performed according to a method commonly used in the art. Non-limiting examples of the fractionation method include a method of obtaining a fraction from the extract by treating an extract obtained by extracting a dried noni fruit with a predetermined solvent.

It is preferable that the type of solvent used to obtain the fraction in the present invention is purified water. When a solvent other than purified water is used, the content of physiologically active substances exhibiting a hangover relieving effect is sharply reduced, and the intended hangover relieving effect may be insufficient or hardly appear.

Ethanol absorbed into the body due to drinking is mainly metabolized in the liver, is oxidized to acetaldehyde and acetate, and is discharged outside the body, and ADH is known to be involved in the process of oxidation from ethanol to acetaldehyde, and ALDH plays a role in the decomposition/oxidation process of acetaldehyde produced by alcohol oxidation.

In the normal alcohol metabolism process, ingested alcohol is absorbed from the stomach or small intestine, enters the blood vessels and is transferred to the liver, and in hepatocytes, alcohol is oxidized to acetaldehyde by the action of alcohol degrading enzyme, and acetaldehyde is decomposed into acetate by the action of acetaldehyde degrading enzyme, which can be decomposed into carbon dioxide and water to be discharged out of the body.

Although the cause of a hangover is not yet clearly known, there are many academic studies on dehydration, the toxic effects of alcohol and alcohol metabolites (acetaldehyde, formaldehyde, acetone, etc.) and nutrient deficiency due to malabsorption of nutrients, and recently, it has been reported that it is caused by acetaldehyde, acetone and the like, which are the metabolites of alcohol (Tomita Y, Haseba T, Kurosu M, Watanabe T (1990). *Arukoru Kenkyut Yakubutsu Ison.* 25(2). 116-128) (Tsukamoto S, Muto T. Nagoya T, Shimamura M, Saito T, Tainaka H. (1989). *Alcohol Alcohol.* 24(2). 101~108).

Therefore, in a specific exemplary embodiment of the present invention, it was attempted to identify a substantial active ingredient showing a hangover relieving efficacy among various physiologically active ingredients of noni, and to prepare an extract or fraction with an increased content thereof. Since it is known that noni contains various polyphenol compounds such as chlorogenic acid, p-anisic acid, gallic acid, epicatechin, caffeic acid and 4-hydroxybenzoic acid, iridoid compounds such as deacetylasperulosidic acid (DAA), asperulosidic acid (ASPA) and asperuloside (ASP), rutin, scopoletin and the like, the ADH activity for each individual component was evaluated, but as confirmed in FIGS. 1 and 2, all of the individual components tested did not show an increase in ADH activity compared to the control group, and thus, it was found that these were not substantial active ingredients.

As it was confirmed that various individual components found to be contained in noni fruit do not affect alcohol decomposition, in another specific exemplary embodiment of the present invention, noni fruit was prepared in various extract forms to increase the effect of enhancing ADH activity for each extract. As confirmed in FIG. 3, the ADH activity was higher in the order of noni fruit hot water extract <50% ethanol noni fruit extract <30% ethanol noni fruit extract <10% ethanol noni fruit extract.

Figure 4:
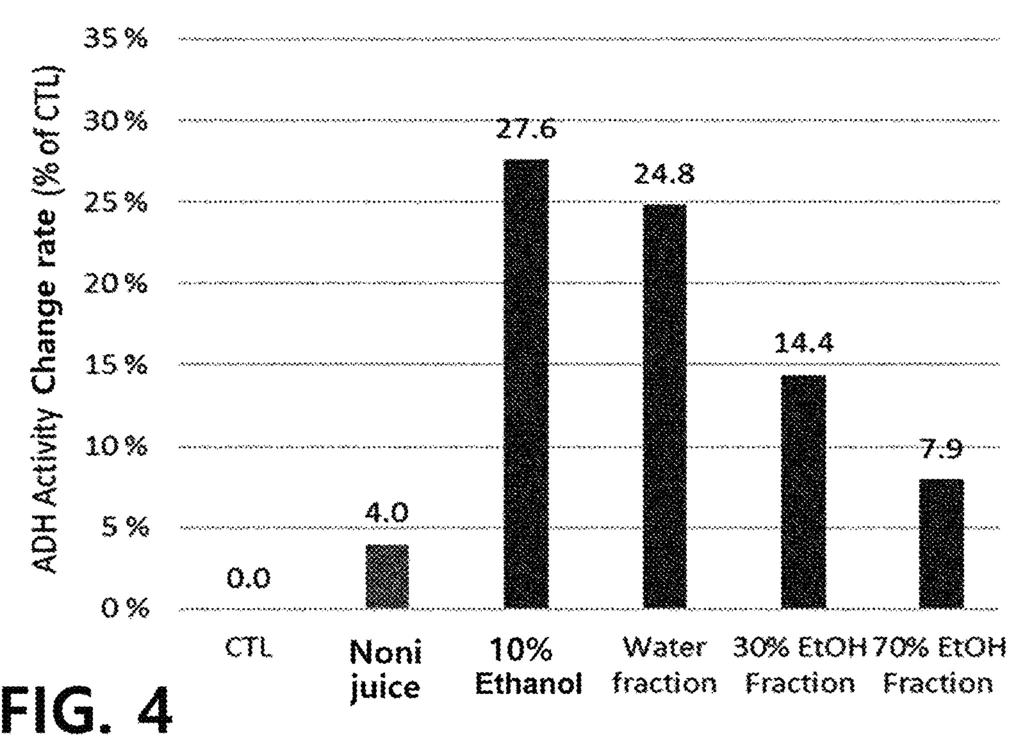
FIG. 4 is a graph showing the measurement of ADH activity of the purified water fraction, 30% ethanol fraction and 70% ethanol fraction with respect to the 10% ethanol noni fruit extract.

In still another specific exemplary embodiment of the present invention, additional fractions were prepared and selected to confirm clear active ingredients from the 10% ethanol noni fruit extract that showed the most excellent ADH activity, and consequently, as shown in FIG. 4, the highest ADH activity was shown in the purified water fraction of the 10% ethanol noni fruit extract, and it was confirmed that most of the ADH activity increasing factors were included in the purified water fraction. In addition, as a result of GPC analysis, as shown in FIG. 5, it was confirmed that substantially active ingredients contained in the purified water fraction were polysaccharides having a molecular weight of 8 kDa to 10 kDa.

Figure 6A:
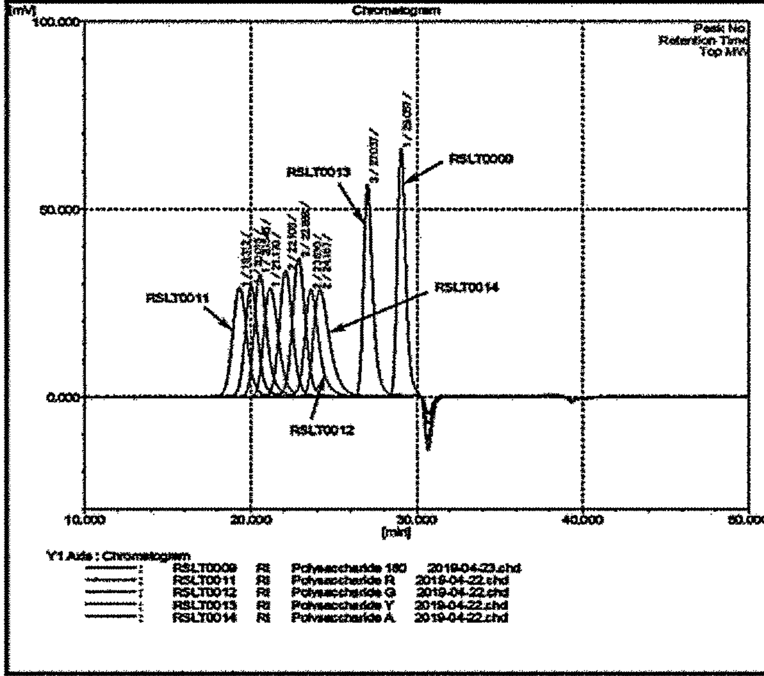
FIGS. 6*a* and 6*b* show in order the GPC results and calibration curves of the polysaccharide standard product (FIG. 6*a*) and the GPC results of the purified water fraction of the 30% ethanol noni fruit extract (FIG. 6*b*).
Figure 6A:
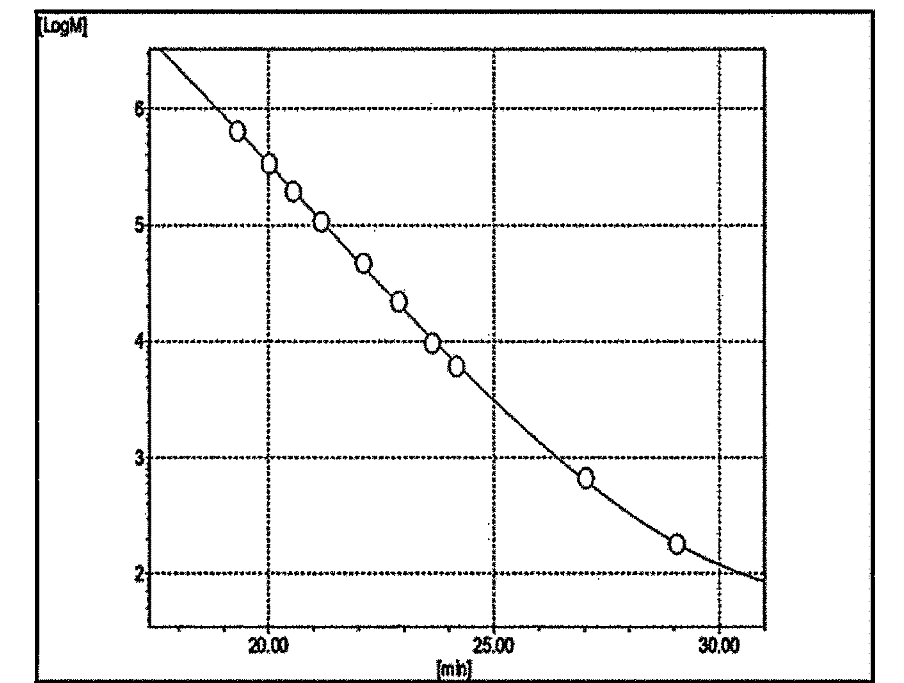

Further, in another specific exemplary embodiment of the present invention, in order to determine whether the difference in efficacy between the 10% ethanol noni fruit extract and the 30% ethanol noni fruit extract is due to the difference in main ingredients, GPC was performed for the purified water fractions of the 30% ethanol noni fruit extract, and as a result of the analysis, as shown in FIG. 6, it was confirmed that polysaccharides having an average molecular weight of 10 kDa or more were mainly included in the purified water fractions of the 30% ethanol noni fruit extract.

When the results of FIGS. 5*a* to 5*b* and FIGS. 6*a* to 6*b* are compared, it was confirmed that the main components of the 10% ethanol noni fruit extract were polysaccharides having an average molecular weight of 8 to 10 kDa, whereas the main components of the 30% ethanol noni fruit extract were polysaccharides having a molecular weight of 10 kDa or more, and thus, it was determined that the ADH activity enhancing effects were different depending on the average molecular weight of the polysaccharide.

In still another specific exemplary embodiment of the present invention, in order to determine whether the ADH activity varies according to the average molecular weight of the polysaccharide, an aged noni juice stock solution, a crude polysaccharide of the aged noni juice stock solution and a water-saturated butanol fraction of the 10% ethanol extract were prepared, and their alcohol-decomposing ability and the average molecular weight of polysaccharides were confirmed.

As confirmed in FIG. 4, the aged noni juice stock solution of Comparative Example 1 did not show an increase in ADH activity compared to the control group which was not treated with the sample, and it showed significantly lower ADH activity compared to the 10% ethanol noni fruit extract and the purified water, 30% ethanol and 70% ethanol fractions thereof. As a result of the GPC analysis, as shown in FIG. 8*b*, polysaccharides having an average molecular weight of 1.0 kDa were mainly included in the noni juice stock solution.

Figure 7A:
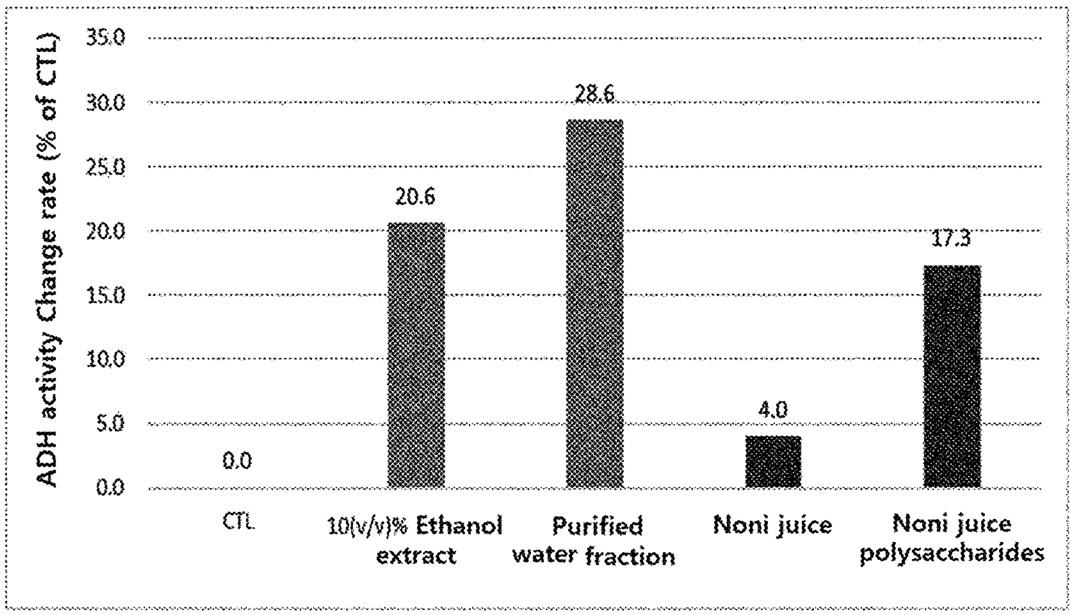
FIG. 7*a* shows the ADH activity of the crude polysaccharide of the aged noni juice stock solution of Comparative Example 1.

As confirmed in FIG. 7*a*, the crude polysaccharides of the aged noni juice stock solution still showed low ADH activity compared to the same dose of the 10% ethanol noni fruit extract and the purified water fraction thereof. As a result of GPC analysis, as confirmed in FIG. 8*c*, polysaccharides having an average molecular weight of 13.2 kDa were mainly included in the crude polysaccharides of the aged noni juice stock solution.

Figure 7B:
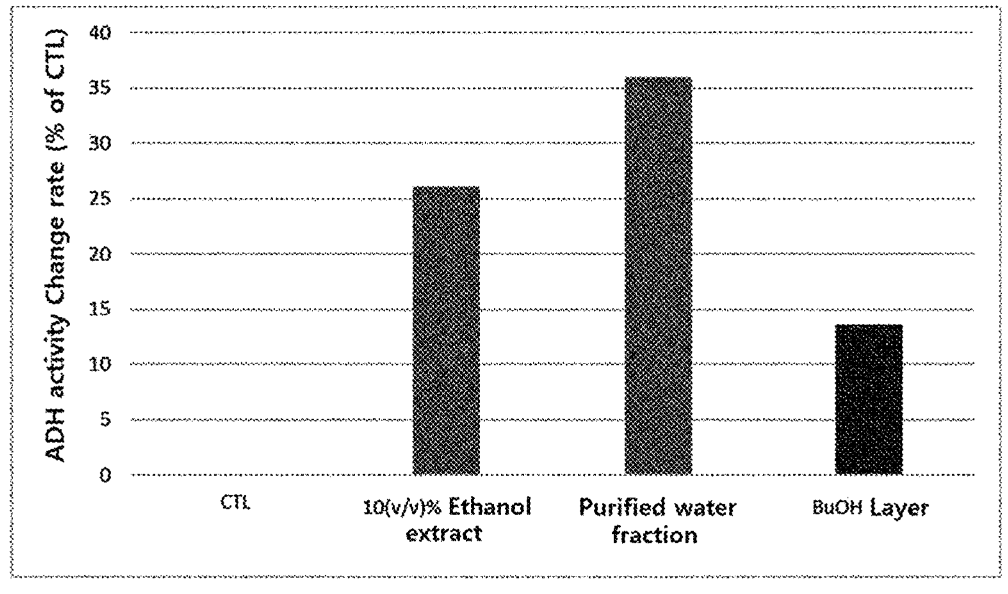
FIG. 7*b* shows the ADH activity of the water-saturated butanol fraction of a noni fruit extract.

As confirmed in FIG. 7*b*, the water-saturated butanol fraction of the 10% ethanol noni fruit extract exhibited significantly lower ADH activity than the 10% ethanol extract and the purified water fractions thereof. As a result of GPC analysis, as shown in FIG. 8*d*, polysaccharides having an average molecular weight of 1.1 kDa were mainly included in the water-saturated fraction.

Through the above results, it was determined that polysaccharides having an average molecular weight of 8 to 10 kDa exhibited excellent alcohol decomposition ability, compared to other average molecular weights.

In a further specific exemplary embodiment of the present invention, in order to verify the hangover relieving effectiveness of the polysaccharide fraction with an average molecular weight of 8 to 10 kDa derived from the noni extract, the polysaccharides in the 10% ethanol noni fruit extract were separated by molecular weight size to determine their ADH decomposition ability. As a result, as confirmed in FIG. 13, it was confirmed that noni-derived polysaccharides, particularly polysaccharides with a size of 8 to 10 kDa, were the active ingredients exhibiting the most excellent hangover efficacy.

Therefore, in the composition of the present invention, the noni fruit ethanol extract and the purified water fractions thereof mainly include polysaccharides having an average molecular weight of 8 kDa to 10 kDa as an active ingredient having a hangover relieving effect.

Figure 14:
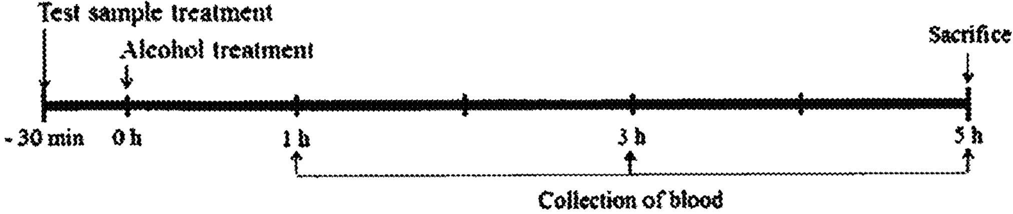
FIG. 14 shows the administration schedule of a sample in the design of an animal experiment to evaluate the hangover relieving efficacy of an ethanol noni fruit extract in vivo.

In a further specific exemplary embodiment of the present invention, the inventors of the present invention administered the noni fruit ethanol extract and alcohol (ethanol) according to the sample administration schedule shown in FIG. 14, and then measured blood ethanol concentration, blood acetaldehyde concentration and ADH and ALDH activities in the liver over time, in order to confirm the in vivo hangover relieving efficacy of the 10% ethanol noni fruit extract including polysaccharides having an average molecular weight of 8 kDa to 10 kDa as a main component.

Figure 15:
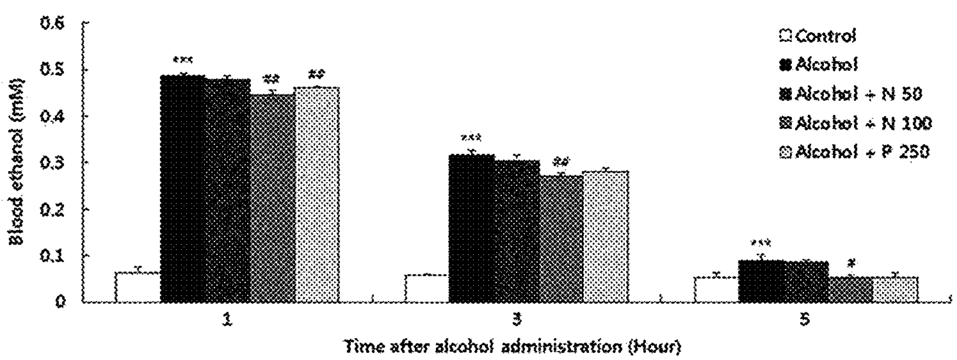
FIG. 15 is a graph showing blood ethanol concentrations measured over time after the administration of a sample and alcohol according to the administration schedule of FIG. 14.
Figure 15:
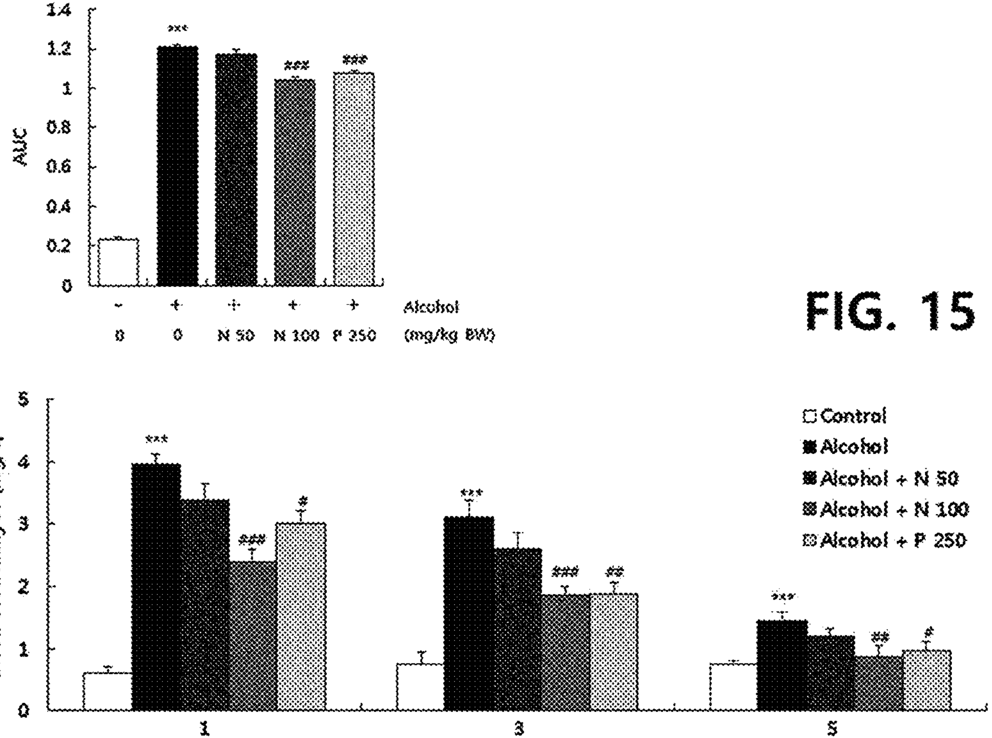
Figure 16:
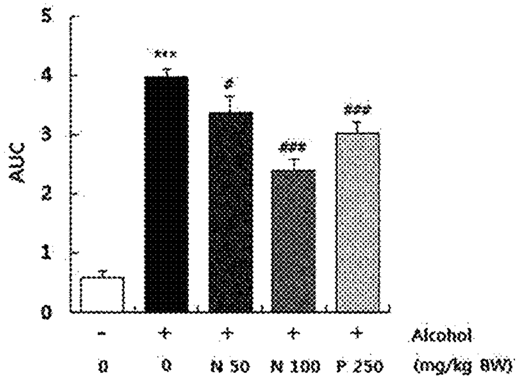
FIG. 16 is a graph showing blood acetaldehyde concentrations measured over time after the administration of a sample and alcohol according to the administration schedule of FIG. 14.
Figure 17:
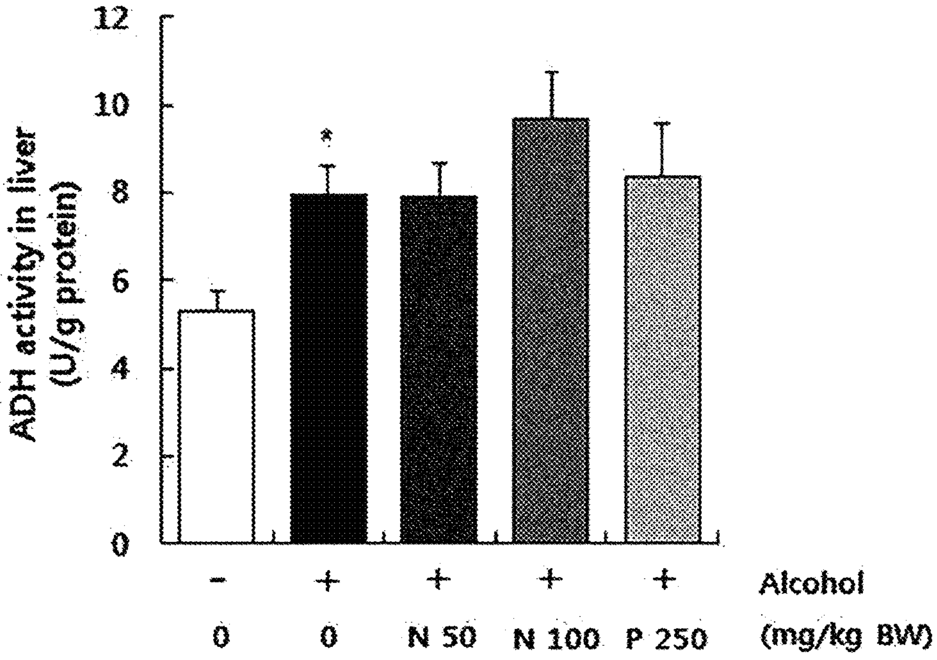
FIG. 17 is a graph showing the activity of ADH and ALDH in the liver by extracting the liver 5 hours after the administration of a sample and alcohol according to the administration schedule of FIG. 14.
Figure 17:
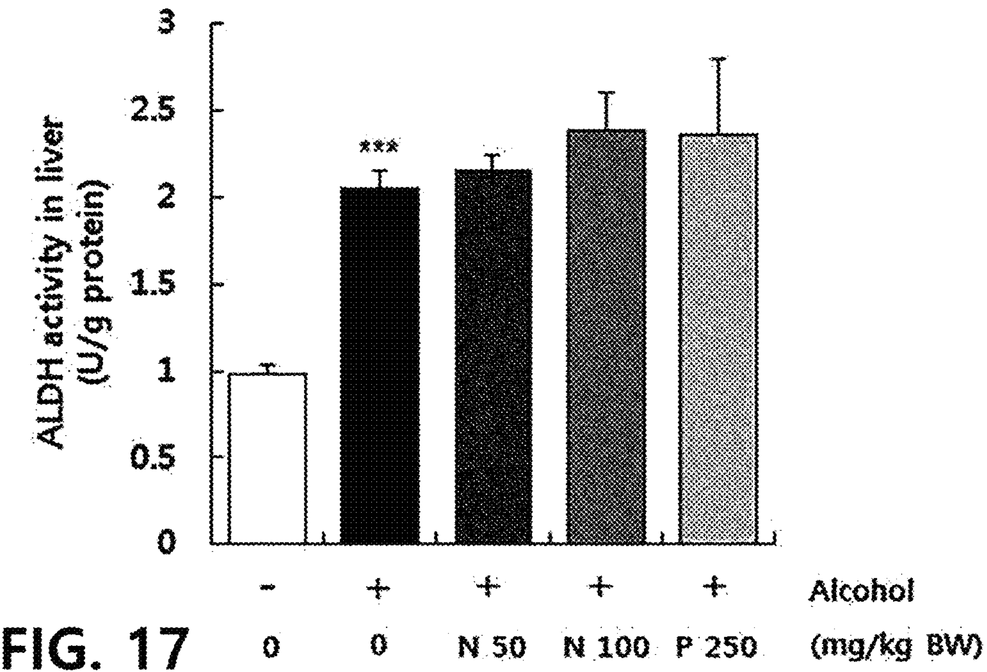

As a result, as shown in FIGS. 15 to 17, it was confirmed that the blood ethanol concentration (FIG. 15) and blood acetaldehyde concentration (FIG. 16) were significantly reduced in a concentration-dependent manner, and the ADH and ALDH activities (FIG. 17) in liver tissue increased in the noni fruit ethanol extract administration group.

Therefore, by enhancing the ADH and/or ALDH activity to effectively remove hangover-causing substances, the noni fruit extract and the fraction thereof including polysaccharides having an average molecular weight of 8 kDa to 10 kDa according to the present invention as main components may improve hangover symptoms such as vomiting, nausea, dizziness, thirst, lethargy, headache, muscle pain, memory loss, heartburn and the like.

A second aspect of the present invention relates to a food composition using the above-described composition for relieving a hangover.

The food composition of the present invention can be understood as a concept including all of the conventional functional food or health functional food.

The health functional food (functional food), which is the same term as food for special health use (FoSHU), refers to food with high medicinal and medical effects to efficiently exhibit a bioregulatory function in addition to a function of nutrient supply. Herein, "function(al)" means controlling nutrients for the structure or functions of the human body or providing beneficial effects to health purposes, such as physiological effects. The food of the present invention may be prepared by a method commonly used in the art, and during the preparation, raw materials and ingredients commonly added in the art may be added to prepare the food. In addition, the food may be prepared in any formulation without limitation, as long as it is acceptable as food. The food composition of the present invention may be prepared in various formulations, and unlike general drugs, it has an advantage in that there is no side effect that may occur when a drug is taken for a long time, because of using the food as a raw material.

The health functional food of the present invention may include 1.0 to 10.0% by weight of a noni fruit ethanol extract and/or a fraction thereof based on the total weight for the purpose of improving a hangover. If the noni fruit ethanol extract and/or the fraction thereof is included at less than 1.0% by weight, the effect of improving hangover may not be sufficiently realized, and if it is included at more than 10.0% by weight, the original quality of the product may not be realized or the cost effectiveness may be reduced.

The functional food may include conventional food additives, and unless otherwise specified, the suitability of the food additives is determined by the specification and standard of the concerned item in accordance with the General Provisions and General Test Methods of the Korea Food Additives Codex authorized by the Korea Food and Drug Administration, unless otherwise specified.

The items described in the Korea Food Additives Codex include, for example, chemical compounds such as ketones, glycine, potassium citrate, nicotinic acid, cinnamic acid and the like, natural additives such as persimmon pigment, licorice extract, crystalline cellulose, kaoliang pigment, guar gum and the like, and mixed preparations such as sodium L-glutamate preparation, noodle additive alkali preparation, preservative preparation, tar color preparation and the like.

The health functional food composition of the present invention includes the form of tablets, granules, powders, capsules, liquid solutions and/or pills, and the food to which the composition of the present invention can be added includes, for example, various foods, for example, beverages, chewing gum, tea, vitamin complexes, health supplements and the like.

Specifically, the functional food in the form of tablets may be prepared by granulating a mixture with a noni fruit ethanol extract and/or a fraction thereof, excipients, binders, disintegrants and other additives by a conventional method, and then compression molding by placing a slip modifier or the like, or by direct compression molding of the mixture. In addition, the functional food in the tablet form may contain a flavoring agent and the like, if necessary, and it may be coated with an appropriate coating agent, if necessary.

Among the functional foods in the form of capsules, hard capsules may be prepared by filling conventional hard capsules with mixtures of eggplant extracts and additives such as excipients, or granular or coated granules thereof, and soft capsules may be prepared by filling a mixture of the noni fruit ethanol extract and/or a fraction thereof with additives such as excipients in capsule bases such as gelatin and the like.

The soft capsules may contain a plasticizer such as glycerin or sorbitol, a colorant, a preservative and the like, if necessary.

The functional food in the form of pills may be prepared by molding a mixture of the noni fruit ethanol extract and/or a fraction thereof, excipients, binders, disintegrants and the like with a proper method, and if necessary, the pills may be coated with white sugar or other proper coating agents, or sparkled with a powder of starch, talc or proper substances, if necessary.

The functional food in the form of granules may be prepared in a granular shape by treating a mixture of the noni fruit ethanol extract or a fraction thereof, and excipients, binders, disintegrants and the like with a proper method, and the granules may include fragrance ingredients, corrigents and the like, if necessary.

In addition, the definitions of the excipients, binders, disintegrants, slip modifiers, corrigents, fragrance ingredients and the like are described in publications known in the art and may include those having the same or similar function As an essential ingredient that can be included in the health functional food composition of the present invention, other ingredients are not particularly limited except for containing the noni fruit ethanol extract or a fraction thereof, and it may contain various herbal extracts, food supplement additives or natural carbohydrates similar to conventional food.

In addition, the food supplement additives include conventional food supplement additives in the art, for example, flavoring agents, corrigents, coloring agents, fillers, stabilizers and the like.

Examples of the natural carbohydrate include monosaccharides such as glucose, fructose and the like; disaccharides such as maltose, sucrose and the like; and polysaccharides such as conventional sugars such as dextrin and cyclodextrin, and sugar alcohols such as xylitol, sorbitol and erythritol. As flavoring agents other than those described above, natural flavoring agents (e.g., rebaudioside A, glycyrhizin, etc.) and synthetic flavoring agents (saccharin, aspartame, etc.) may be advantageously used.

In addition to the above, the health functional food composition of the present invention may contain a variety of nutritional supplements, vitamins, minerals (electrolytes), flavoring agents such as synthetic flavoring agents, natural flavoring agents and the like, coloring agents and fillers (cheese, chocolate, etc.), pectic acid and a salt thereof, alginic acid and a salt thereof, organic acids, protective colloid thickeners, pH adjusters, stabilizers, preservatives, glycerin, alcohols, carbonation agents used in carbonated drinks and the like. Besides, it may contain pulp for the production of natural fruit juices, fruit juice drinks and vegetable drinks. These components may be used independently or in combination.

A third aspect of the present invention relates to a method for relieving a hangover, including administering an effective amount of a composition including polysaccharide having an average molecular weight of 8 kDa to 10 kDa which is derived from a noni fruit extract, or a noni fruit extract or a fraction thereof including the polysaccharide to a subject in need thereof.

In the method for relieving a hangover according to the present invention, since the descriptions for the characteristics and effects of a composition including polysaccharide having an average molecular weight of 8 kDa to 10 kDa which is derived from a noni fruit extract, or a noni fruit extract or a fraction thereof including the polysaccharide are the same as described above, the descriptions thereof will be omitted.

As used herein, the term "administration" means providing a given composition of the present invention to a subject by any suitable method.

The preferred dosage of the composition of the present invention varies depending on the subject's condition and weight, the degree of hangover, the formulation form of the composition and the like, but it may be appropriately selected to achieve the intended effect of relieving the hangover.

As used herein, the term "effective amount" refers to an amount of the noni fruit extract or a fraction thereof which is sufficient to reduce or completely resolve hangover symptoms such as vomiting, nausea, dizziness, thirst, lethargy, headache, muscle pain, memory loss and heartburn, by enhancing the ADH and/or ALDH activity to effectively remove the substances that cause a hangover. For desirable effects, the composition of the present invention may be administered once or several times before or after drinking or while drinking.

In the method for relieving a hangover according to the present invention, the composition may be administered to a subject by various routes, and preferably, it may be orally administered. In addition, it may be used alone or in combination with other methods to relieve a hangover.

A fourth aspect of the present invention relates to the use of a composition including polysaccharide having an average molecular weight of 8 kDa to 10 kDa which is derived from a noni fruit extract, or a noni fruit extract or a fraction thereof including the polysaccharide in the manufacture of a medicament or food for relieving a hangover.

Similarly, in terms of the use of the present invention, since the descriptions for the characteristics and effects of a composition including polysaccharide having an average molecular weight of 8 kDa to 10 kDa which is derived from a noni fruit extract, or a noni fruit extract or a fraction thereof including the polysaccharide are the same as described above, the descriptions thereof will be omitted.

Hereinafter, the present invention will be described in more detail through examples. These examples are only for illustrating the present invention, and it will be apparent to those of ordinary skill in the art that the scope of the present invention is not to be construed as being limited by these examples.

Modes of the Invention

Preparation Example 1

Preparation of Noni Fruit Extract Using 10 (v/v) % Ethanol

After checking and selecting whether there were foreign substances mixed in the processed and dried noni fruit, the dried noni fruit was pulverized into 40 to 100 mesh to increase extraction efficiency. After placing 10 (v/v) % ethanol at 10 times the weight of the pulverized product into the extractor, the dried noni fruit pulverized product was slowly added as a raw material. After the input of the raw material was completed, extraction was carried out at a temperature of 80° C. with stirring for 4 hours. Thereafter, filtration was performed by using Whatman No. 4 paper filter paper. The filtered extract was concentrated under reduced pressure at 60 to 70° C. to prepare a concentrate, and then, it was freeze-dried to prepare in the form of powder.

Preparation Example 2

Preparation of Fractions of 10 (v/v) % Ethanol Noni Fruit Extract

A 10 to 20 Brix concentrate obtained by concentrating the 10 (v/v) % ethanol extract of Preparation Example 1 under reduced pressure at 60 to 70° C. was introduced into an open column filled with HP-20 resin, and it was fractionated and purified for each compartment under the conditions of purified water, 30% ethanol and 70% ethanol as an eluate solution.

Comparative Example 1

Preparation of Aged Noni Juice Stock Solution

An Indonesian fermented and aged noni stock solution (UD. Herbali, Importer Asel) at 6.5 Brix or higher was obtained from online and used.

Comparative Example 2

Preparation of Noni Fruit Extract Using Hot Water

A noni fruit extract was prepared in the same manner as in Preparation Example 1, except that hot water was used as the extraction solvent.

Comparative Example 3

Preparation of Noni Fruit Extract Using 30 (w/w) % Ethanol

A noni fruit extract was prepared in the same manner as in Preparation Example 1, except that 30 (w/w) % ethanol was used as the extraction solvent.

Comparative Example 4

Preparation of Factions of 30 (w/w) % Ethanol Noni Fruit Extract

A 10 to 20 Brix concentrate obtained by concentrating the 30 (w/w) % ethanol extract of Preparation Example 2 under reduced pressure at 60 to 70° C. was introduced into an open column filled with HP-20 resin, and it was fractionated and purified by using purified water as an eluate solution.

Comparative Example 5

Preparation of Noni Fruit Extract Using 50 (v/v) % Ethanol

A noni fruit extract was prepared in the same manner as in Preparation Example 1, except that 50 (v/v) % ethanol was used as the extraction solvent.

Comparative Example 6

Preparation of Noni Fruit Extract Using 70 (v/v) % Ethanol

A noni fruit extract was prepared in the same manner as in Preparation Example 1, except that 70 (v/v) % ethanol was used as the extraction solvent.

Comparative Example 71

Preparation of Noni Fruit Extract Using 95 (v/v) % Ethanol

A noni fruit extract was prepared in the same manner as in Preparation Example 1, except that 95 (v/v) % ethanol was used as the extraction solvent.

Comparative Example 81

Preparation of Oriental Raisin Tree Extract

Oriental raisin fruit extract powder SR-23853 was obtained from Saerom B&F Co., Ltd. and used. This product contains the Oriental raisin fruit concentrate (solids 11%): dextrin at a ratio of 80:20.

The materials obtained in Preparation Examples 1 to 2 and Comparative Examples 1 to 8 are summarized in Table 1.

TABLE 1

| Preparation Example/ Comparative Example | Obtained materials |
|---|---|
| Preparation Example 1 | 10 (v/v)% ethanol noni fruit extract |
| Preparation Example 2 | Purified water of 10 (v/v)% ethanol noni fruit extract, 30% ethanol and 70% ethanol fractions |
| Comparative Example 1 | Aged noni juice stock solution |
| Comparative Example 2 | Nono fruit hot water extract |
| Comparative Example 3 | 30 (w/w)% ethanol noni fruit extract |
| Comparative Example 4 | Fractions of purified water of 30 (w/w)% ethanol noni fruit extract |
| Comparative Example 5 | 50 (v/v)% ethanol noni fruit extract |
| Comparative Example 6 | 70 (v/v)% ethanol noni fruit extract |
| Comparative Example 7 | 90 (v/v)% ethanol noni fruit extract |
| Comparative Example 8 | Dextrin-containing Oriental raisin fruit extract |

Example 1

Identification of Active Ingredients in Noni Extract

The inventors of the present invention tried to identify a substantial active ingredient showing hangover relieving efficacy among various components in the noni extract, and to prepare an extract with an increased content thereof. Since it is already known that noni contains various polyphenol compounds, as well as iridoid, rutin, scopoletin and the like, ADH activity was evaluated in this example for individual components isolated from noni.

1-1. Determination of Alcohol Decomposition Ability of Polyphenol Compounds

To this end, the alcohol dehydrogenase (ADH) activity enhancing efficacy of polyphenol compounds found to be contained in noni such as chlorogenic acid, p-anisic acid, gallic acid, epicatechin, caffeic acid and 4-hydroxybenzoic acid was measured.

The ADH activity was measured by referring to [Bergmeyer, H. U. 1974. Methods of enzymatic analysis. Academic Press, New York. pp. 28], and measurements were made according to the method presented herein. All samples were treated at 10 μM, and the ADH activity of each sample was expressed as relative activity (%) with respect to the control group, based on 100% of the activity of the control group (CTL) which was not treated with the sample.

As a result, as confirmed in FIG. 1, the ADH activity of all samples did not show an increase compared to the control group, and accordingly, it was found that various polyphenol compounds of noni were not substantial active ingredients exhibiting the hangover relieving efficacy.

1-2. Determination of Alcohol Decomposition Ability of Rutin, Scopoletin and Iridoid The ADH activity enhancing efficacy of rutin, scopoletin and three iridoid compounds such as deacetylasperulosidic acid (DAA), asperulosidic acid (ASPA) and asperuloside (ASP) found to be contained in noni was measured in the same manner as in Example 1-1. All samples were treated at 10 μM, and the ADH activity of each sample was expressed as relative activity (%) with respect to the control group, based on 100% of the activity of the control group (CTL) which was not treated with the sample.

Figure 2:
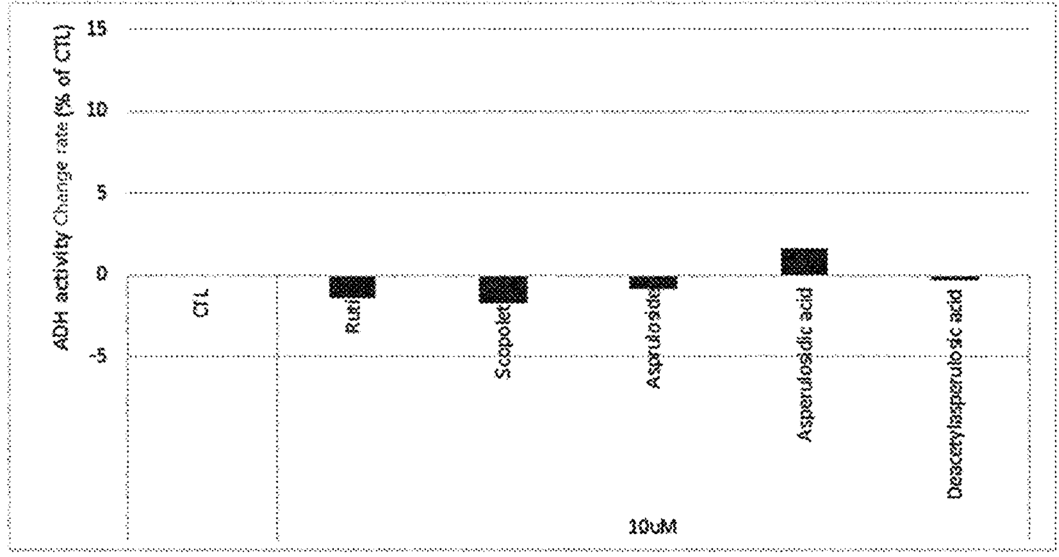
FIG. 2 shows the results of measuring the efficacy of enhancing the ADH activity by rutin, scopoletin and three types of iridoid compounds such as deacetylasperulosidic acid (DAA), asperulosidic acid (ASPA) and asperuloside (ASP), which are known to be included in noni.

As a result, as confirmed in FIG. 2, rutin, scopoletin and all three types of iridoid compounds did not show an increase in ADH activity compared to the control group, and accordingly, it was found that rutin, scopoletin, and three types of iridoid compounds of noni are not substantial active ingredients that exhibit the hangover relieving efficacy.

Example 2

Determination of Alcohol Decomposition Ability of Noni Fruit Extract

As it was confirmed that various individual components found to be contained in noni fruit did not affect alcohol decomposition, noni fruit was prepared in various extract forms in this example, and the ADH activity enhancing efficacy of each extract was confirmed.

To this end, in this example, the ADH activity enhancing efficacy of each extract prepared in Preparation Example 1 and Comparative Examples 2, 3 and 5 to 7 was measured in the same manner as in Example 1-1, and all samples were treated at 100 μg/mL and 200 μg/mL, and by setting a sample that was not treated with the noni fruit extract as the control group, the activity of ADH of the samples was expressed as relative activity (%) with respect to the control group.

Figure 3:
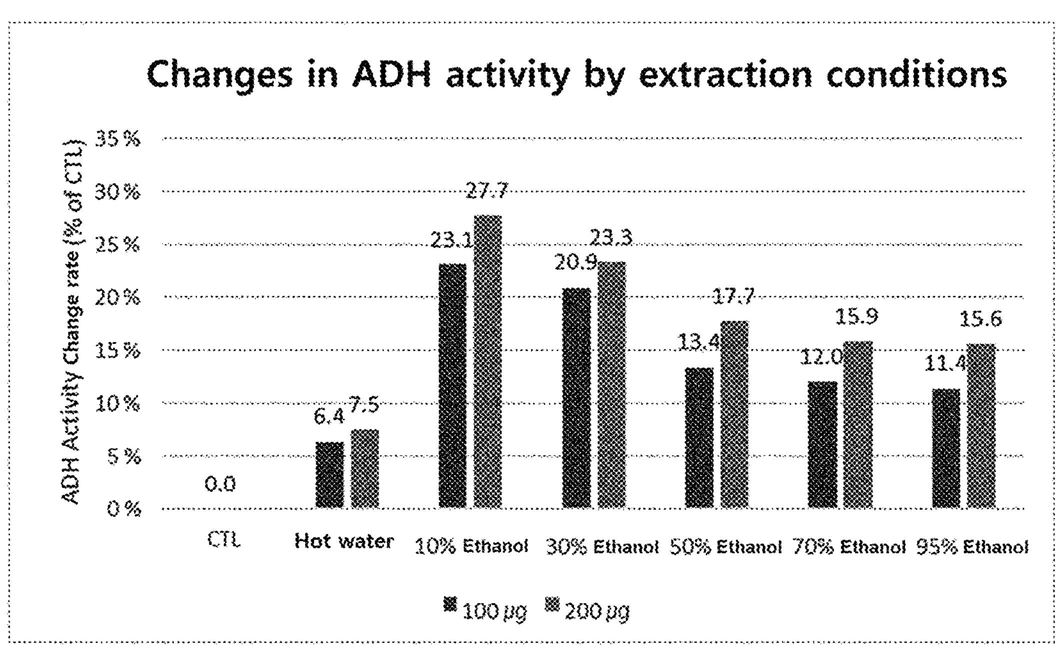
FIG. 3 is a graph showing changes in ADH activity of the noni fruit extract according to the concentration of ethanol as an extraction solvent.

As a result, as confirmed in FIG. 3, ADH activity was found to be higher in the order of noni fruit hot water extract <50 (v/v) % ethanol noni fruit extract <30 (w/w) % ethanol noni fruit extract <10 (v/v) % ethanol noni fruit extract.

Example 3

Determination of Alcohol Decomposition Ability for Fractions of 10 (v/v) % Ethanol Noni Fruit Extract and Confirmation of Active Ingredient Thereof 3-1. Determination of Alcohol Decomposition Ability of Fractions of Noni Fruit Extract in 10 (v/v) % Ethanol In order to confirm a clear active ingredient in the 10 (v/v) % ethanol noni fruit extract of Preparation Example 1, which showed the most excellent ADH activity, additional fractions were prepared and selected as in Preparation Example 2.

The alcohol decomposition ability of each of the purified water fraction, 30% ethanol fraction and 70% ethanol fraction of 10 (v/v) % ethanol noni fruit extract was evaluated by measuring the ADH activity in the same manner as in Example 1-1, and as an additional comparative group, the ADH activity of the Indonesian aged noni juice of Comparative Example 1 was also evaluated. All samples were treated at 100 μg/mL.

As a result, as shown in FIG. 4, the highest ADH activity was shown in the purified water fraction of 10 (v/v) % ethanol noni fruit extract, which confirmed that that most of the ADH activity increasing factors were included in the purified water fraction.

3-2. GPC Analysis of Purified Water Fraction of Noni Fruit Extract in 10 (v/v) % Ethanol In order to confirm the substance substantially showing the efficacy in the purified water fraction for which most of the ADH activity enhancing efficacy was confirmed, gel permeation chromatography (GPC) analysis was performed. Table 2 shows the analysis conditions.

TABLE 2

| Classification | Detailed contents |
|---|---|
| Device | Tosh Co. EcoSEC HLC-8320 GPC |
| Detector | RI-Detector |
| Column | Tskgel guard PWxl + 2 × TSKgel GMPWxl + TSKgel G2500PWxl (7.8 × 300 mm) |
| Mobile phase | 0.1M $NaNo_3$ |
| Flow rate | 1.0 mL/min |
| Infusion capacity | 200 μL, 3 mg/mL |
| Oven temperature | 40° C. |

Figure 5A:
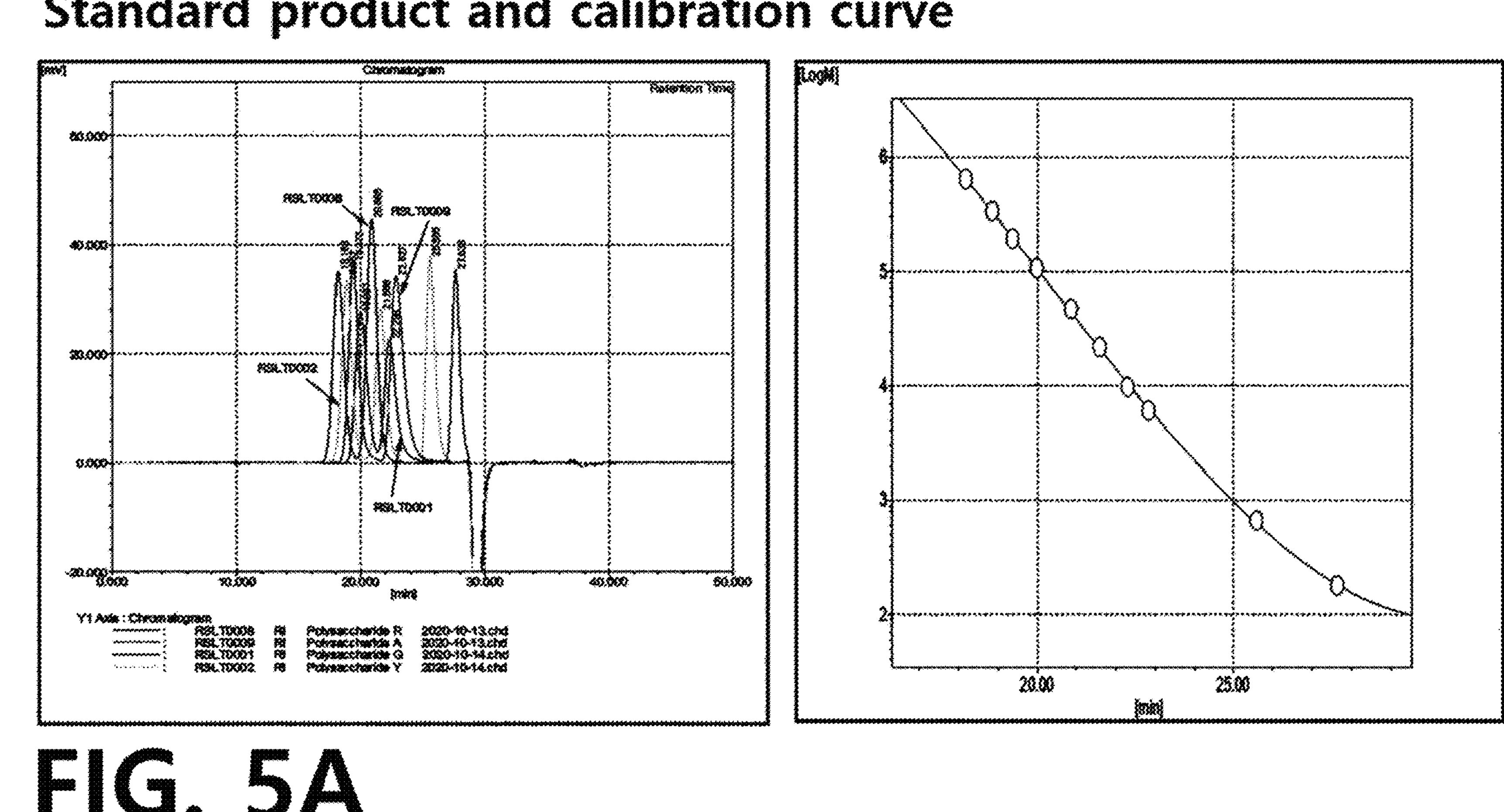
FIGS. 5*a* and 5*b* show in order the results and calibration curves of gel permeation chromatography (GPC) of a polysaccharide standard product (FIG. 5*a*), and the GPC results for the 10% ethanol noni fruit extract purified water fraction (FIG. 5*b*).
Figure 5B:
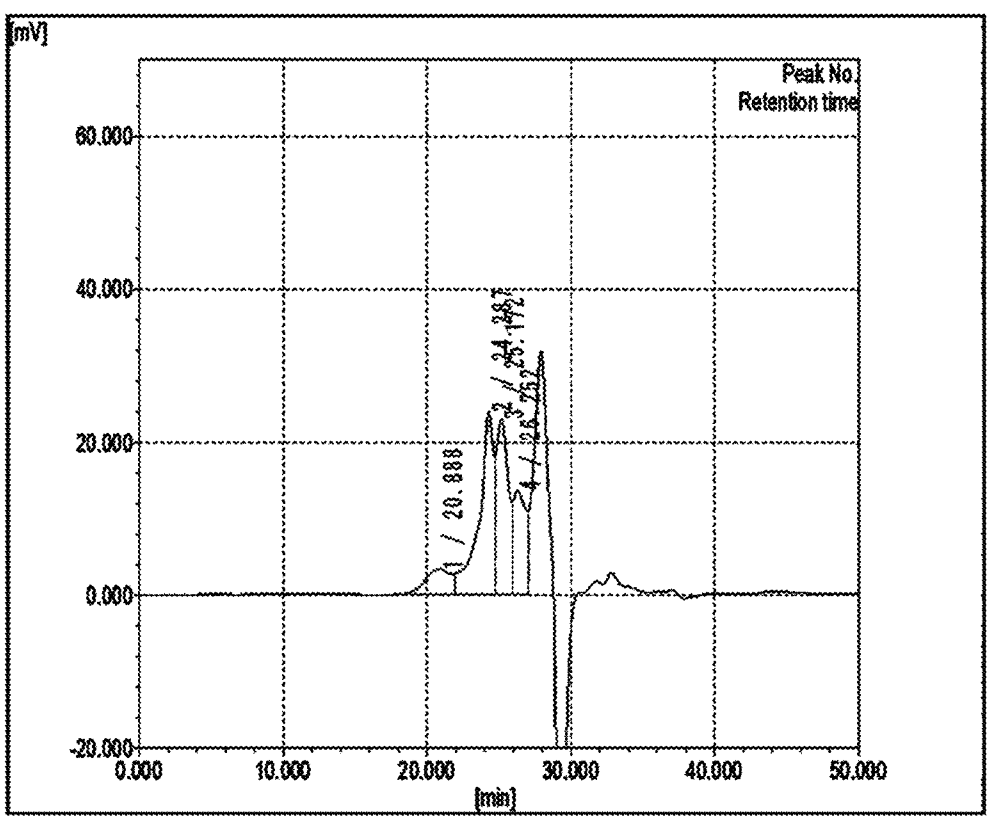

The GPC results of the purified water fractions of pullulan (Agilent pullulan polysaccharide kit, PL2090-0101) used as a standard material and the 10 (v/v) % ethanol noni fruit extract are shown in FIGS. 5*a* and 5*b*, respectively. As confirmed in FIGS. 5*a* and 5*b*, polysaccharides having an average molecular weight of 8 to 10 kDa were included in the purified water fraction, and it was confirmed that these polysaccharides were substantially active ingredients for enhancing the ADH activity.

Example 4

Confirmation of Components of 30 (w/w) % Ethanol Noni Fruit Extract

In order to confirm that the difference in the efficacies of the 10 (v/v) % ethanol noni fruit extract of Preparation Example 1 and the 30 (w/w) % ethanol noni fruit extract of Comparative Example 3 as confirmed in FIG. 2 is due to the difference in the main components, GPC analysis was performed on the purified water fraction of the 30 (w/w) % ethanol noni fruit extract in the same manner as in Example 3-2. The purified water fraction of the 30 (w/w) % ethanol noni fruit extract is the same as described in Comparative Example 4.

Figure 6B:
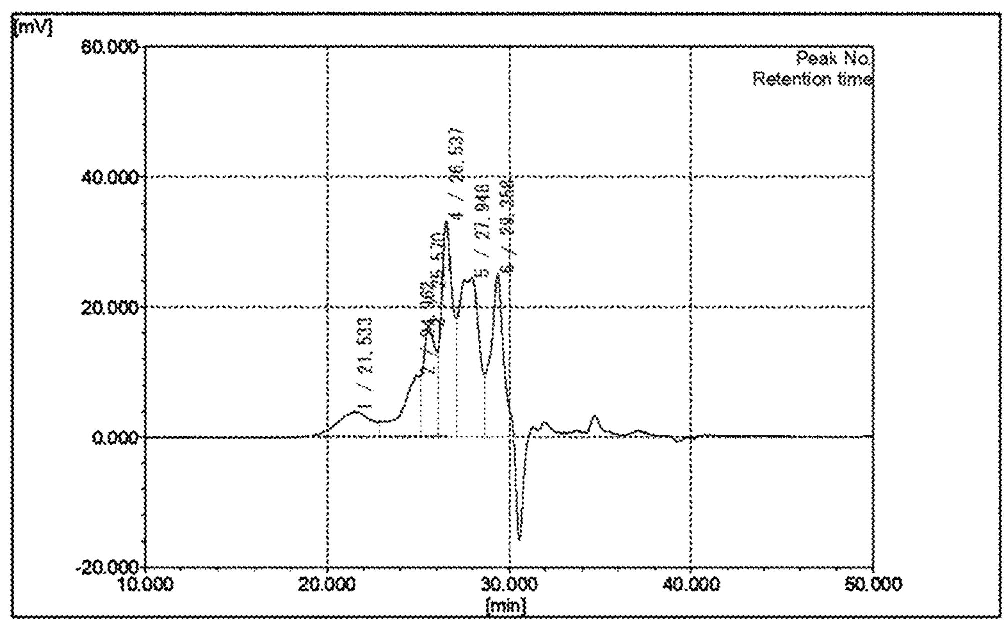

The GPC results of the purified water fractions of pullulan (Agilent pullulan polysaccharide kit, PL2090-0101) used as a standard material and the 30 (w/w) % ethanol noni fruit extract are shown in FIGS. 6*a* and 6*a*, respectively. As shown in FIGS. 6*a* and 6*b*, it was confirmed that polysaccharides having an average molecular weight of 10 kDa or more were mainly included in the purified water fraction of the 30 (w/w) % ethanol noni fruit extract.

When the results of FIGS. 5*a* to 5*b* and FIGS. 6*a* to 6*b* are compared, it was confirmed that the main components of the 10 (v/v) % ethanol noni fruit extract were polysaccharides having an average molecular weight of 8 to 10 kDa, whereas the main components of the 30 (w/w) % ethanol noni fruit extract were polysaccharides having an average molecular weight of 10 kDa or more, and thus, it was determined that the ADH activity enhancing effects were different depending on the average molecular weight of the polysaccharide.

Example 5

Confirmation of Components of Aged Noni Juice Stock Solution

In order to confirm whether the difference in efficacy between the 10 (v/v) % ethanol noni fruit extract of Preparation Example 1 and the aged noni juice stock solution of Comparative Example 1 as confirmed in FIG. 4 is due to the difference in main components, GPC analysis was performed on the aged noni juice stock solution similarly in the same manner as in Example 3-2.

Figure 8A:
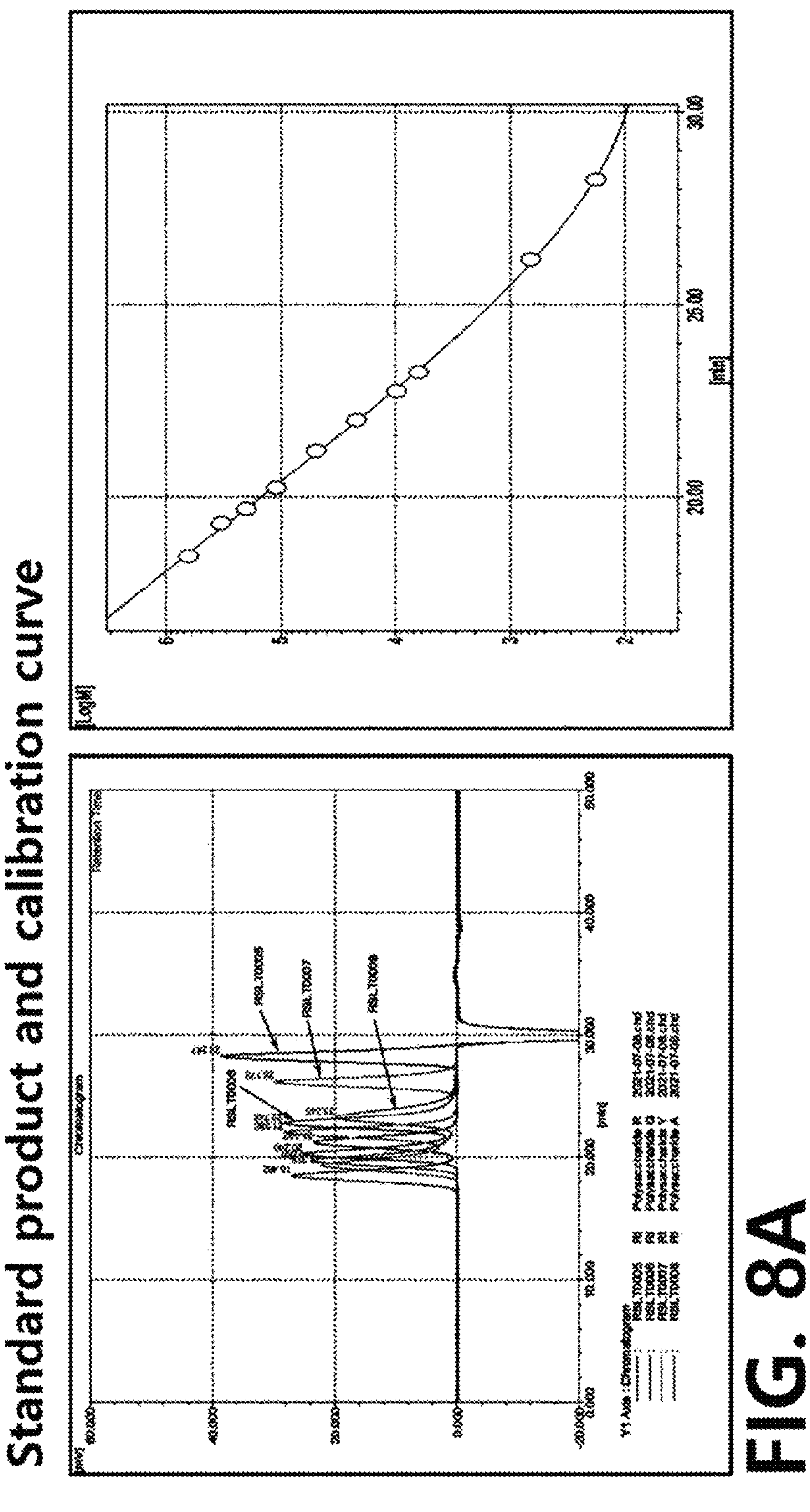
FIG. 8*a* shows the GPC results and calibration curves of a polysaccharide standard product.
Figure 8B:
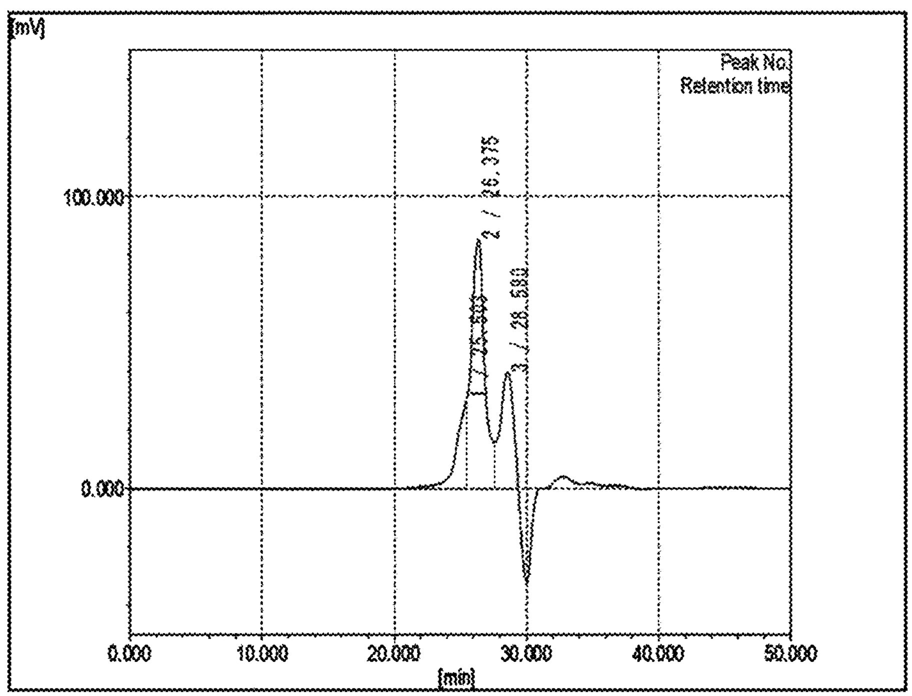
FIGS. 8*b* to 8*d* show in order the GPC results of the noni juice stock solution (FIG. 8*b*), the crude polysaccharide of the noni juice stock solution (FIG. 8*c*) and the water-saturated butanol fraction (FIG. 8*d*).

The GPC results of pullulan (Agilent pullulan polysaccharide kit, PL2090-0101) used as a standard material and the aged noni juice stock solution are shown in FIGS. 8*a* and 8*b*, respectively. As shown in FIGS. 8*a* and 8*b*, the noni juice stock solution mainly included polysaccharides having an average molecular weight of 1.0 kDa.

When the results of FIGS. 5*a* to 5*b*, 6*a* to 6*b* and 8*a* to 8*b* are compared, it was confirmed that the main components of the 10 (v/v) % ethanol noni fruit extract were polysaccharides having an average molecular weight of 8 to 10 kDa, and the main components of the 30 (w/w) % ethanol noni fruit extract were polysaccharides with an average molecular weight of 10 kDa or more, whereas the main components of the noni juice stock solution were polysaccharides with an average molecular weight of 1.0 kDa, and thus, it was confirmed that the results are consistent with the results of Example 3 that the ADH activity enhancing efficacies are significantly different depending on the average molecular weight of polysaccharide.

Example 6

Measurement of Alcohol Decomposition Ability of Noni Extracts or Fractions Containing Polysaccharides with Various Average Molecular Weights Through the results of Examples 4 and 5, it was found that the main active ingredient showing the hangover relieving efficacy in the noni extract is polysaccharide, but the alcohol decomposition ability is significantly different depending on the average molecular weight of the polysaccharide. Accordingly, in this example, various types of noni extracts or fractions containing polysaccharides in high concentrations were prepared, and their alcohol decomposition ability and average molecular weight of polysaccharides were determined.

6-1. Preparation of Crude Polysaccharides from Aged Noni Juice Stock Solution

The aged noni juice stock solution of Comparative Example 1 was precipitated with 95% ethanol at 4° C. for 12 hours to prepare crude polysaccharides of the aged noni juice.

6-2. Measurement of Alcohol Decomposition Ability of Crude Polysaccharides in Aged Noni Juice Stock Solution The ADH activity was measured in the same manner as in Example 1-1 to measure the alcohol decomposition ability of crude polysaccharides of the aged noni juice stock solution prepared in Example 6-1, and as comparative groups, the ADH activities of the 10 (v/v) % ethanol noni fruit extract of Preparation Example 1, the purified water fraction of the 10 (v/v) % ethanol noni fruit extract of Preparation Example 2 and the Indonesian aged noni juice of Comparative Example 1 were also evaluated.

As confirmed in FIG. 7*a*, the 10 (v/v) % ethanol noni fruit extract and the purified water fraction thereof exhibited the ADH activity which was 5 to 7 times higher compared to the same amount of noni juice and 1.2 to 1.7 times higher compared to the noni juice crude polysaccharides.

6-3. Preparation of Water-Saturated Butanol Fraction of 10 (v/v) % Ethanol Noni Fruit Extract A 10 to 20 Brix concentrate obtained by concentrating the 10 (v/v) % ethanol extract of Preparation Example 1 under reduced pressure at 60 to 70° C. was placed in a separatory funnel, and then, water-saturated butanol having a volume 1 to 2 times the volume of the concentrate was introduced, and it was mixed by shaking vigorously, and afterwards, the two solvents were allowed to separate for about 30 minutes. Thereafter, only the water-saturated butanol in the upper layer in which the polysaccharides were dissolved in the solvent separated into two layers was separated/concentrated and used as a fraction.

6-4. Determination of Alcohol Decomposition Ability of Water-Saturated Butanol Fraction of 10 (v/v) % Ethanol Noni Fruit Extract In order to measure the alcohol decomposition ability of the water-saturated butanol fraction of the ethanol 10 (v/v) % noni fruit extract prepared in Example 6-3, the ADH activity was measured in the same manner as in Example 1-1, and as comparative groups, the ADH activities of the purified water fraction of the 10 (v/v) % ethanol noni fruit extract of Preparation Example 1 and the purified water fraction of the 10 (v/v) % ethanol noni fruit extract of Preparation Example 2 were also evaluated.

As confirmed in FIG. 7*b*, the water-saturated butanol fraction exhibited significantly lower ADH activity than the 10 (v/v) % ethanol extract and the purified water fraction thereof.

6-5. Identification of Components

In order to confirm the main components of the crude polysaccharide of the aged noni juice stock solution prepared in Example 6-1 and the water-saturated butanol fraction of the ethanol 10 (v/v) % noni fruit extract prepared in Example 6-3, GPC analysis was performed in the same manner as in Example 3-2. The results of GPC analysis for the standard material are shown in FIG. 8*a*.

Figure 8C:
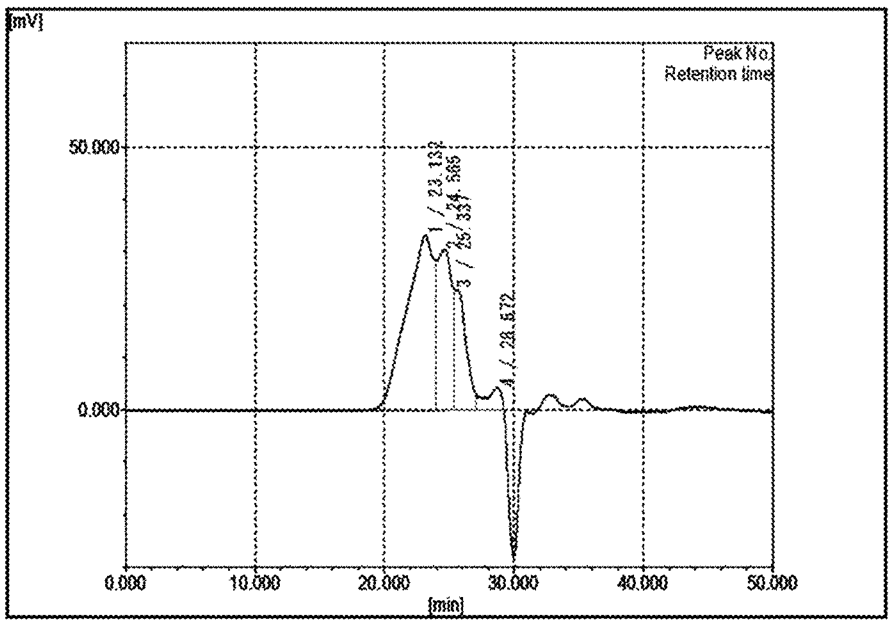
Figure 8D:
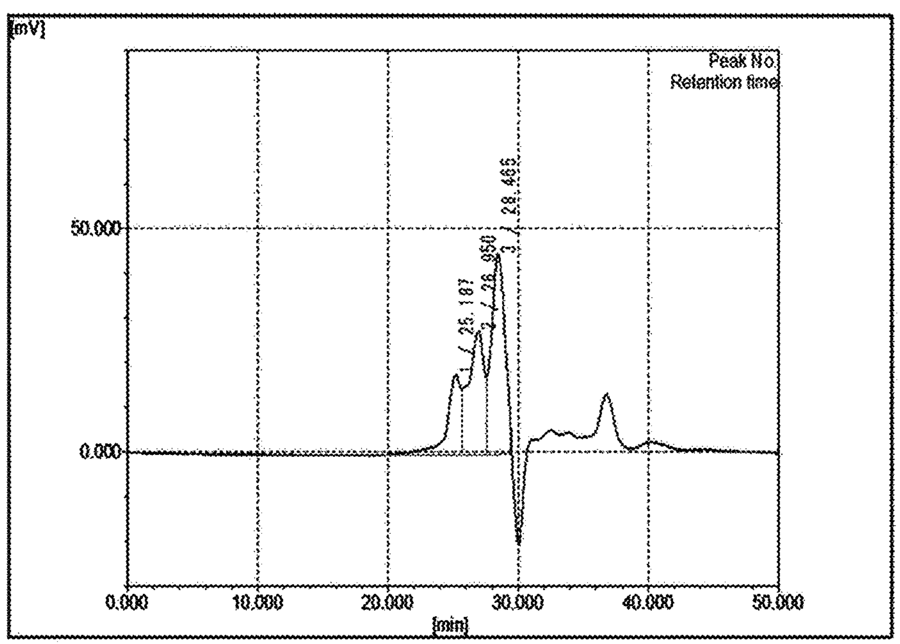

As a result of GPC analysis, as confirmed in FIG. 8*c*, the crude polysaccharide of the aged noni juice stock solution mainly included polysaccharides having an average molecular weight of 13.2 kDa, and as confirmed in FIG. 8*d*, the water-saturated fraction mainly included polysaccharides having an average molecular weight of 1.1 kDa. Through the above results, it was determined that polysaccharides having an average molecular weight of 8 to 10 kDa exhibited excellent alcohol decomposition ability, compared to other average molecular weights.

Example 7

Confirmation of Hangover Relieving Effectiveness of Noni Extract-Derived Polysaccharide Fraction Having Average Molecular Weight of 8 to 10 kDa 7-1. Separation of Fractions by Size of Polysaccharide Molecular Weight When the results of Examples 1 to 6 are summarized, the inventors of the present invention believed that polysaccharides among various components in noni affect the hangover relieving efficacy, but the efficacy may vary significantly depending on the average molecular weight of the polysaccharide, and particularly, it was determined that polysaccharides having an average molecular weight of 8 to 10 kDa exhibited excellent efficacy in decomposing alcohol.

Based on these experimental results, the inventors of the present invention tried to separate polysaccharides in the 10 (v/v) % ethanol noni fruit extract by molecular weight size, and t determine the alcohol decomposition ability of each fraction.

Figure 9:
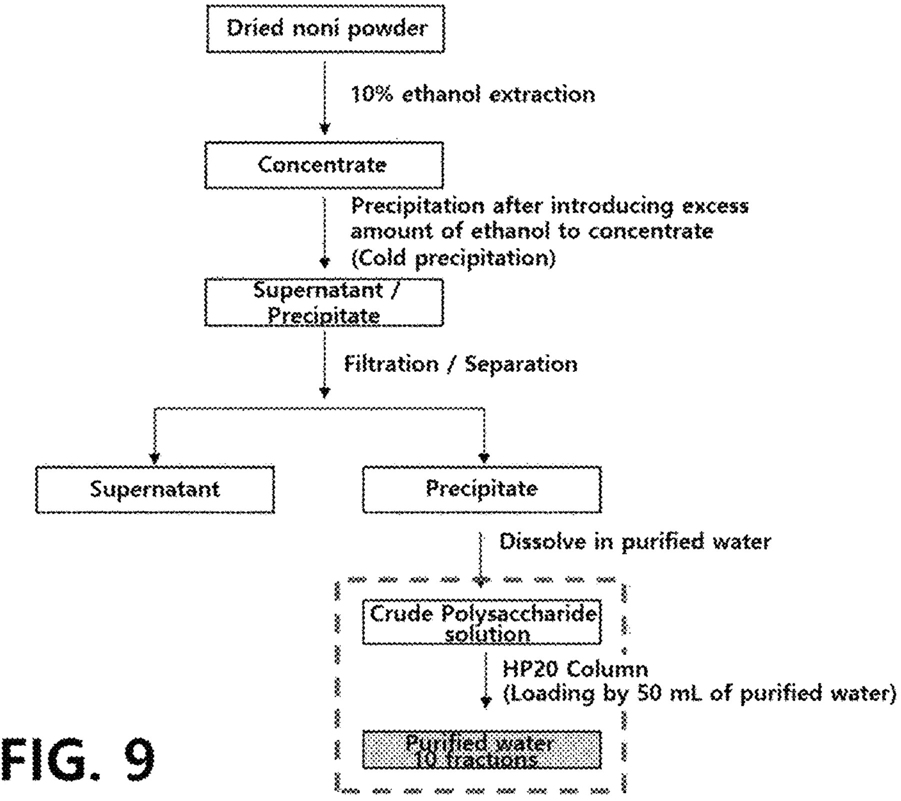
FIG. 9 is a schematic diagram showing a method for preparing fractions by polysaccharide size from a 10% ethanol noni fruit extract.
Figure 10:
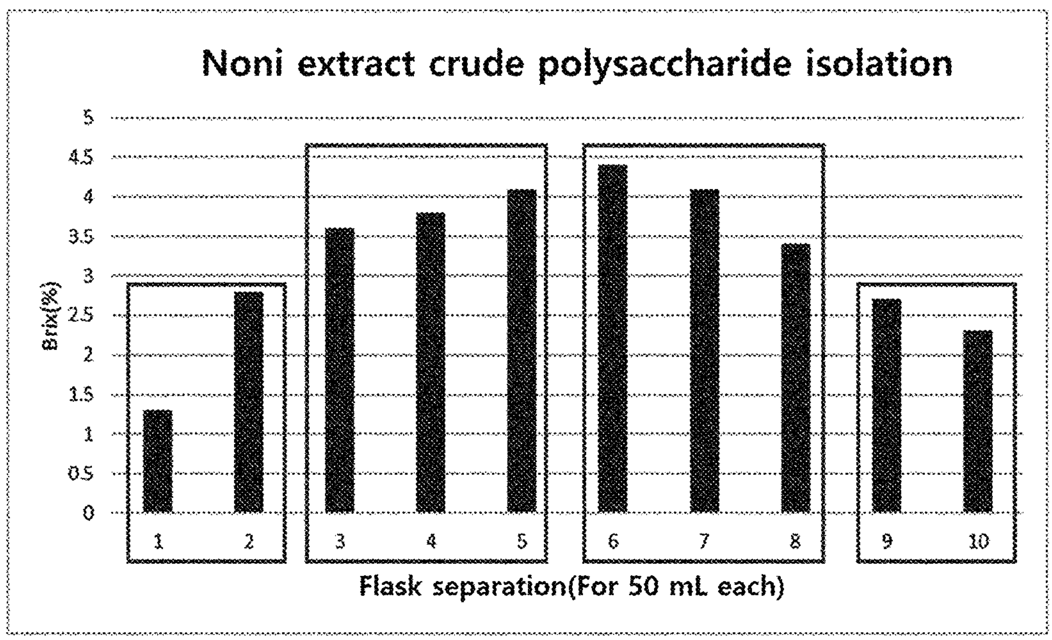
FIG. 10 shows a grouping of a total of 10 fractions obtained by the method of FIG. 9 based on the difference in Brix and properties.

To this end, as shown in FIG. 9, a 10 to 20 Brix concentrate obtained by concentrating the 10 (v/v) % ethanol extract under reduced pressure at 60 to 70° C. was placed into an open column filled with HP-20 resin, and purified water was used as the eluent solution was used to fractionate by 50 mL each. As shown in FIG. 10, a total of 10 fractions obtained were grouped based on differences by Brix and properties, and freeze-drying was performed. The detailed description of the fractions grouped into four is shown in Table 3.

TABLE 3

| Sample name | Expected ingredient | Other |
|---|---|---|
| Fraction 1 | Separation of crude | Fractions from Flasks 1-2 |
| Fraction 2 | polysaccharide | Fractions from Flasks 3-5 |
| Fraction 3 | | Fractions from Flasks 6-8 |
| Fraction 4 | | Fractions from Flasks 9-10 |

Figure 11A:
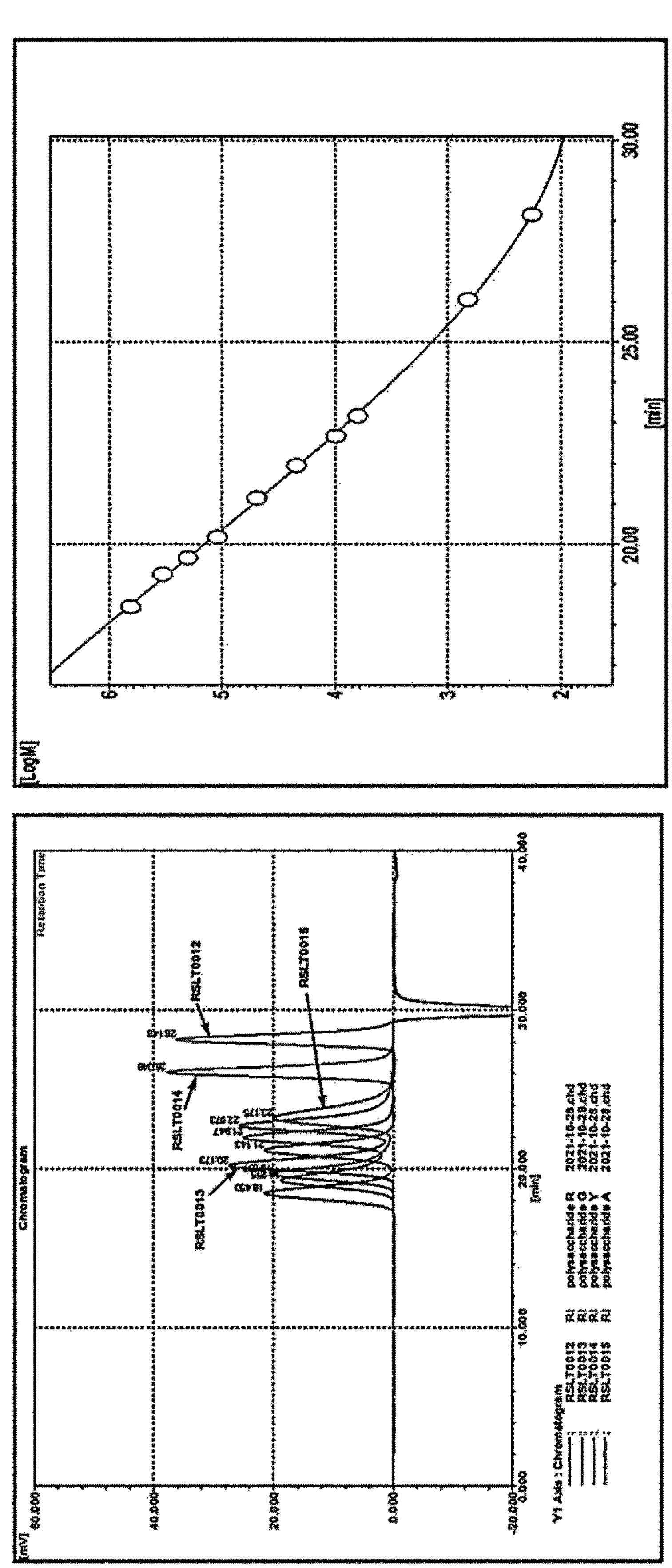
FIG. 11*a* shows the GPC results and calibration curves of pullulan (Agilent pullulan polysaccharide kit, PL2090-0101) used as a standard material.
Figure 11B:
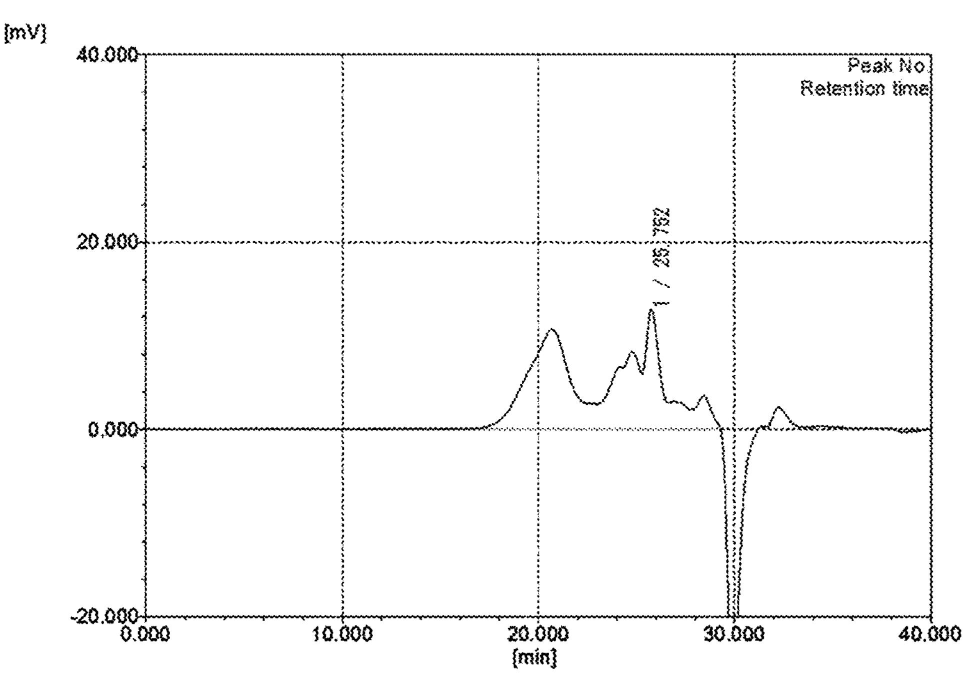
FIGS. 11*b* to 11*e* show the GPC results in the order of four fractions (Fractions 1 to 4) separated according to the grouping of FIG. 10.
Figure 11C:
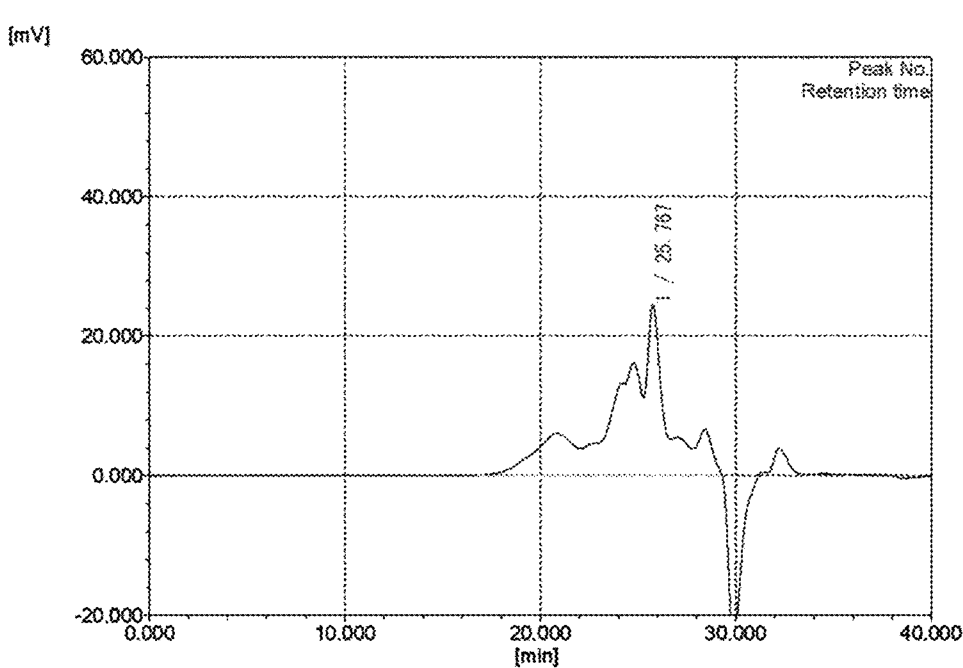
Figure 11D:
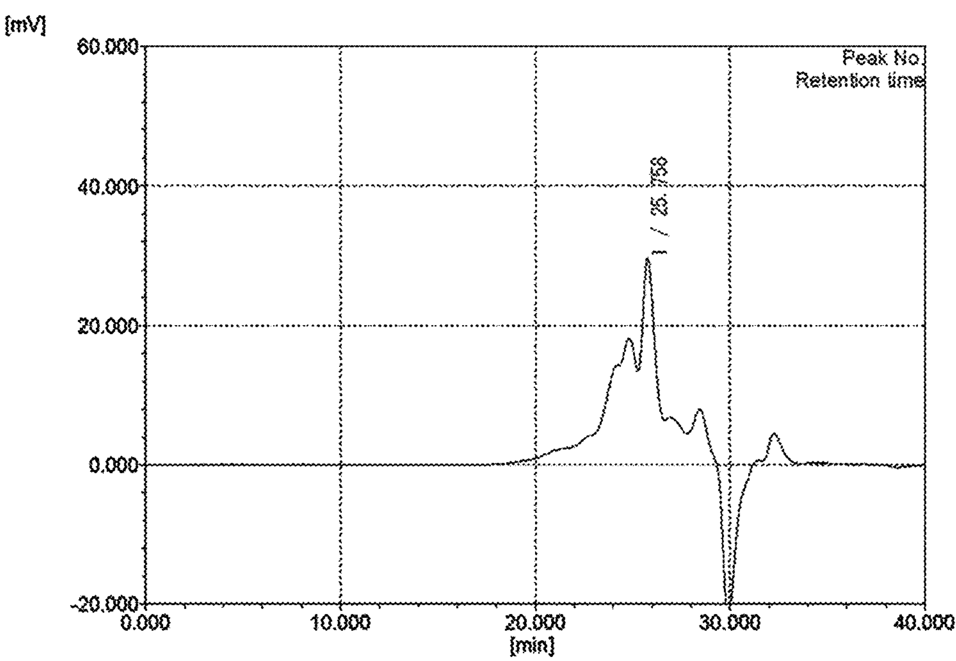
Figure 11E:
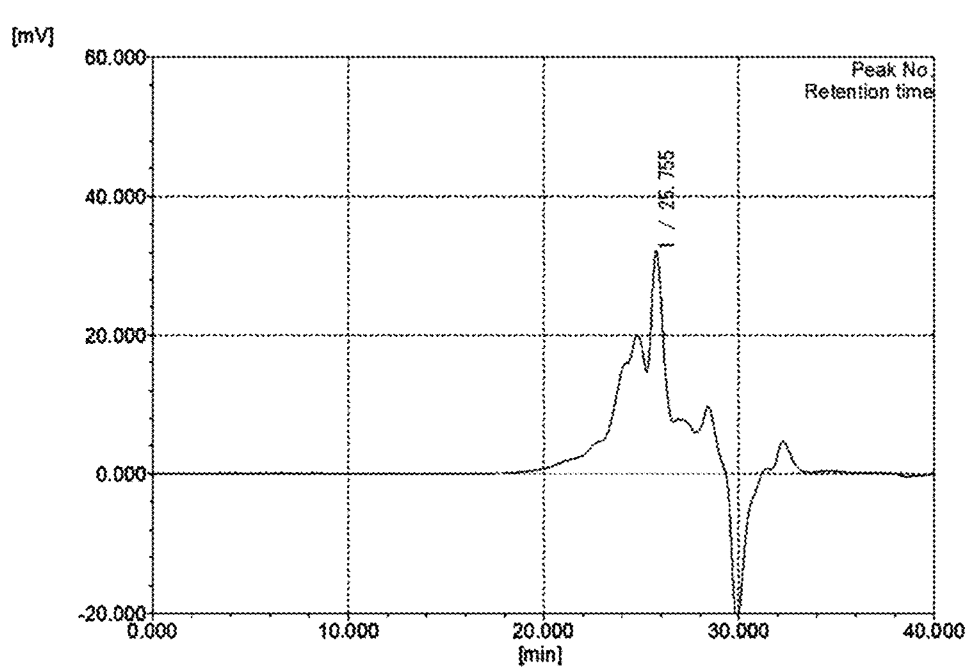

GPC was performed under the conditions shown in Table 4 to determine the average molecular weight of the polysaccharide contained in each sample, and FIG. 11*a* shows the GPC results and calibration curves of pullulan (Agilent pullulan polysaccharide kit, PL2090-0101) used as a standard material, FIGS. 11*b* to 11*e* show the GPC results in the order of the four samples in Table 3, and FIG. 12 shows the average molecular weights of the polysaccharides included in the four samples (Fractions 1 to 4) compared to dextran.

TABLE 4

| Classification | Detailed contents |
|---|---|
| Device | Tosh Co. EcoSEC HLC-8320 GPC |
| Detector | RI-Detector |
| Column | Tskgel guard PWxl + 2 × TSKgel GMPWxl + TSKgel G2500PWxl (7.8 × 300 mm) |
| Mobile phase | 0.1M $NaNo_3$ |
| Flow rate | 1.0 mL/min |
| Infusion capacity | 100 μL, 3 mg/mL |
| Oven temperature | 40° C. |

AS confirmed in FIGS. 11*b* to 11*e* and 12, the average molecular weights of the polysaccharides included in the fractions decreased from Fraction 1 to Fraction 4, and it was confirmed that Fraction 3 included polysaccharide having an average molecular weight of 8.4 kDa.

7-2. Measurement of Alcohol Decomposition Ability by Size of Polysaccharide Molecular Weight For the four samples in Table 3, the ADH activity was measured in the same manner as in Example 1-1.

Figure 13:
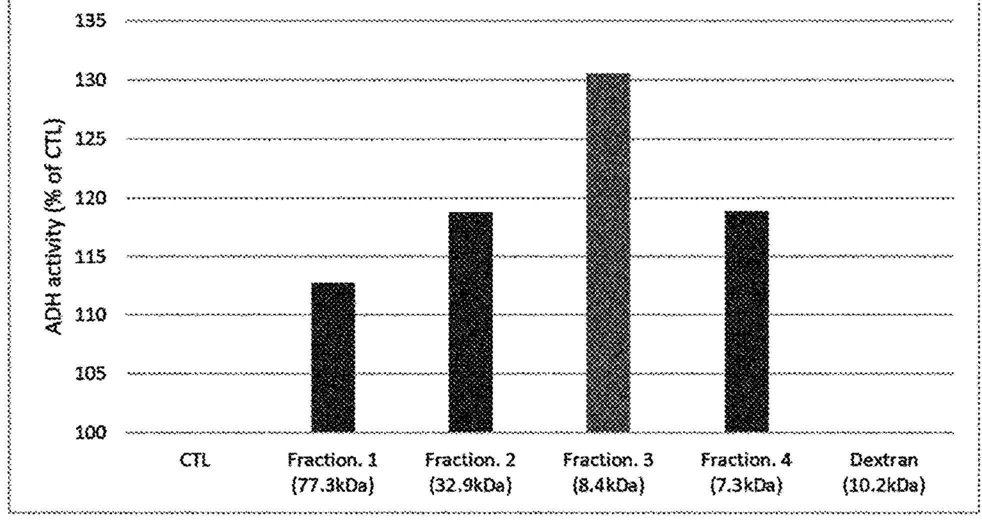
FIG. 13 shows the ADH activity of Fractions 1 to 4 and dextran of FIG. 10.

As confirmed in FIG. 13, the highest ADH activity was shown in Fraction 3 including polysaccharides having an average molecular weight of 8 to 10 kDa. Therefore, it was confirmed that the component showing the most excellent hangover relieving efficacy in the polysaccharides of the noni extract was the polysaccharide of 8 to 10 kDa.

Example 8

Confirmation of Specificity of Hangover Relieving Effect of Polysaccharides Having an Average Molecular Weight of 8 to 10 kDa in Noni Extract In order to confirm whether all polysaccharides having an average molecular weight of 8 to 10 kDa exhibit the excellent hangover relieving efficacy, the ADH activity was measured in the same manner as in Example 1-1, using dextran having an average molecular weight of 9 to 11 kDa as a comparison group. The ADH activity of dextran is shown in FIG. 13, and the GPC results for confirming the average molecular weight of dextran are shown in FIG. 11*f*. The results of GPC analysis for the standard material are shown in FIG. 11*a*.

As confirmed in FIG. 13, even if the size of the polysaccharide is close to 8 to kDa, not all polysaccharides exhibit the hangover relieving efficacy, and noni-derived polysaccharides, particularly, polysaccharides having a size of 8 to 10 kDa, are the active ingredient exhibiting the most excellent hangover relieving efficacy.

Example 9

Confirmation of Hangover Relieving Ability of Noni Fruit Extract and the Fraction Thereof In Vivo In this example, the 10 (v/v) % ethanol noni fruit extract including polysaccharides having an average molecular weight of 8 to 10 kDa, which exhibited the most excellent ADH activity in the in vitro experiments, was evaluated for hangover relieving ability in vivo.

9-1. Experimental Design

Five-week-old SD rats (purchased from Dooyeol Biotech Co., Ltd.) were quarantined and acclimatized for one week, and then, 10 rats were randomly assigned to each group, and samples were treated as shown in Table 5 below.

TABLE 5

| Group | Treatment of rats |
|---|---|
| Normal control group (Normal control) | — |
| Alcohol administration group (Control) | 40% diluted ethanol was administered at 3 g/kg b.w. |
| Noni fruit extract + alcohol administration group | 10 (v/v)% ethanol noni fruit extract was administered at 50 mg/kg b.w. + 40% diluted ethanol was administered at 3 g/kg b.w. |
| | 10 (v/v)% ethanol noni fruit extract was administered at 100 mg/kg b.w. + 40% diluted ethanol was administered at 3 g/kg b.w. |
| Oriental raisin tree fruit extract + alcohol administration group | Oriental raisin tree extract was administered at 250 mg/kg b.w. + 40% diluted ethanol was administered at 3 g/kg b.w. |

The sample administration schedule is shown in FIG. 14. Specifically, 50 mg and 100 mg of the 10 (v/v) % ethanol noni fruit extract of Preparation Example 1 were orally administered to the noni fruit extract administration group+ alcohol administration group, respectively, and after 30 minutes, alcohol (40% fermented ethanol, 3 g/kg)) was orally administered. According to the same dosing schedule, 250 mg of the dextrin-containing Oriental raisin tree fruit extract of Comparative Example 8 was orally administered to the Oriental raisin tree fruit extract+alcohol administration group. Blood was collected from the rats in each group at 1 hour, 3 hours and 5 hours after alcohol administration, respectively.

9-2. Measurement of Blood Alcohol and Acetaldehyde Levels

The concentrations of blood alcohol and acetaldehyde in the blood collected in Example 8-1 were respectively measured as follows.

First of all, after separating the serum from the blood, the concentration of ethanol in the serum was measured by using an ethanol measurement kit (Abcam) according to the method suggested by the manufacturer. The serum was appropriately diluted by using an assay buffer to take 0.05 mL, and then, 0.05 mL of a reaction mix preparation was added and reacted for 1 hour, and then, absorbance was measured at 570 nm. The ethanol content in the serum was calculated by using a standard curve prepared using an ethanol standard solution. Further, in order to evaluate the relationship between serum ethanol concentrations over time, the area under the concentration-time curve (Area under the curve, AUC) was calculated according to the trapezoid rule.

The acetaldehyde concentration in serum was measured by using an acetaldehyde measurement kit (Megazyme) according to the method suggested by the manufacturer. 0.02 mL of buffer and 0.02 mL of NAD+ solution were mixed with 0.05 mL of serum, and after reacting for 2 minutes, absorbance was measured (A1) at 340 nm. 0.005 mL of alcohol dehydrogenase was added thereto, followed by reacting for 4 minutes, and absorbance was measured (A2) at 340 nm. The acetaldehyde content in serum was calculated by the following formula.

$$C(g\ \text{acetaldehyde}/L)=(\Delta A_{sample}/\Delta A_{standard})\times g/L\ \text{standard}\times F$$

$$\Delta A_{sample}=\text{Sample}(A2-A1)$$

$$\Delta A_{standard}=\text{Standard}(A2-A1)$$

$$F=\text{Dilution factor} \quad \text{[Formula]}$$

In addition, the area under the concentration-time curve (AUC) was calculated to evaluate the relationship of serum acetaldehyde concentrations over time.

As a result, as shown in FIGS. 15 and 16, it was confirmed that the concentrations of ethanol and acetaldehyde in the blood were significantly decreased in a concentration-dependent manner of the noni fruit extract in the noni fruit extract administration group+alcohol administration group. In addition, although the administration amount of the sample was smaller in the noni fruit extract+alcohol administration group than in the Oriental raisin tree fruit extract+alcohol administration group, the effect of reducing blood alcohol and acetaldehyde was found to be more excellent.

9-3. Measurement of Alcohol Dehydrogenase and Aldehyde Dehydrogenase Activity

In the administration schedule of FIG. 14, the rats were sacrificed 5 hours after alcohol administration, and liver tissue was extracted. The activities of alcohol dehydrogenase (ADH) and aldehyde dehydrogenase (ALDH) were measured in the extracted liver tissue, respectively.

The ADH activity was measured in the same manner as in Example 1-1, and the ALDH activity was measured according to the protocol using an Aldehyde dehydrogenase activity colorimetric assay kit (BioVision).

As confirmed in FIG. 17, the ADH and ALDH activities in liver tissue increased depending on the treatment concentrations of the noni extract. Similarly, although the administration amount of the sample was smaller in the noni fruit extract administration group+alcohol administration than in the Oriental raisin tree extract+alcohol administration group, the effects of enhancing the ADH and ALDH activities were found to be more excellent.

Accordingly, it was confirmed that the 10 (v/v) % ethanol noni fruit extract including polysaccharides having an average molecular weight of 8 to 10 kDa as the main component acted on overall alcohol metabolism in the body, thereby exhibiting the excellent hangover relieving ability.

The foregoing description of the present invention is intended for exemplifications, and it will be understood by those skilled in the art that the present invention may be easily modified in other specific forms without changing the technical idea and or essential features of the present invention. Therefore, it should be understood that the exemplary embodiments described above are illustrative in all aspects and not restrictive.

The invention claimed is:

1. A method for relieving a hangover, comprising administering an effective amount of a noni fruit extract, the noni fruit extract consisting of polysaccharides having an average molecular weight of 8 kDa to 10 kDa, wherein the polysaccharides are obtained from a noni fruit ethanol extract extracted with 10 to 20% ethanol.

2. The method of claim 1, wherein the polysaccharides exhibit the following effects (a) to (d):

(a) enhancing the activity of alcohol dehydrogenase;

(b) enhancing the activity of aldehyde dehydrogenase;

(c) reducing blood alcohol concentration; and (d) reducing the concentration of acetaldehyde in the blood.

3. The method of claim 1, wherein the polysaccharides are administered in the form of a food composition or a health functional food composition.

* * * * *